Figure 1:
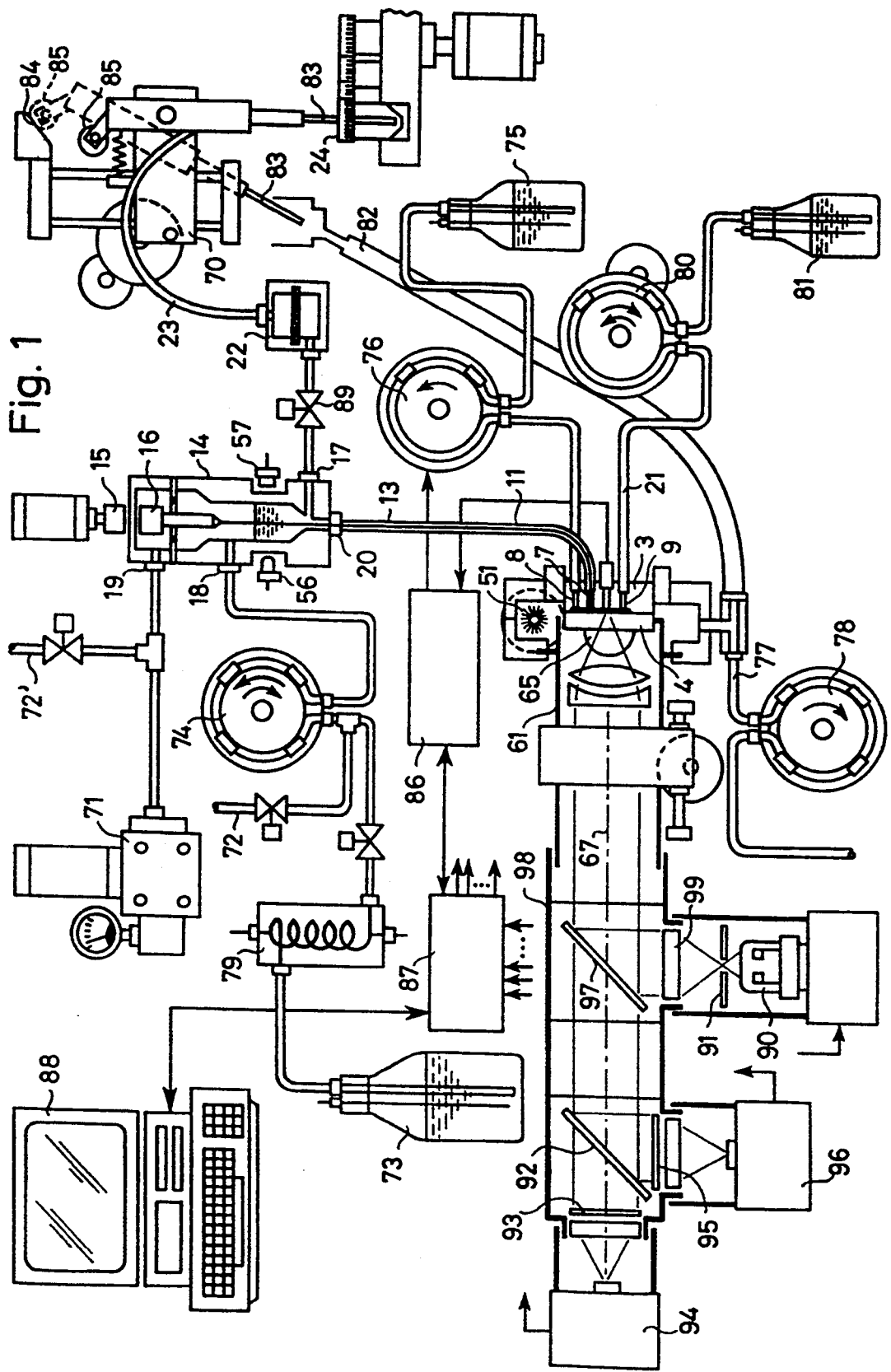

United States Patent [19]

Spinell

[11] Patent Number: 5,351,118
[45] Date of Patent: Sep. 27, 1994

[54] APPARATUS AND METHOD FOR ANALYZING PARTICLES SUSPENDED IN A LIQUID

[75] Inventor: Max Spinell, Hilleroed, Denmark

[73] Assignee: Biometic ApS c/o Dansk Udviklingsfinansiering A/S, Soeborg, Denmark

[21] Appl. No.: 688,545
[22] PCT Filed: May 6, 1991
[86] PCT No.: PCT/DK91/00120
§ 371 Date: Jun. 10, 1991
§ 102(e) Date: Jun. 10, 1991
[87] PCT Pub. No.: WO91/17422
PCT Pub. Date: Nov. 14, 1991

[30] Foreign Application Priority Data
May 4, 1990 [DK] Denmark ............... 1119/90

[51] Int. Cl.$^5$ ................ G01N 21/01; G01N 21/05
[52] U.S. Cl. ............................. 356/72; 356/335; 356/336; 356/337; 356/338; 356/246; 250/283; 422/81; 422/103; 436/805; 436/806
[58] Field of Search ............... 356/335, 336, 337, 338, 356/72, 73, 39, 244, 246; 250/283; 422/62.1, 81, 103; 436/810, 805, 806; 324/71.4

[56] References Cited

U.S. PATENT DOCUMENTS

| | | | |
|---|---|---|---|
| 2,656,508 | 10/1953 | Coulter | 324/71.1 |
| 3,705,876 | 12/1972 | Amann et al. | 528/232 |
| 3,714,565 | 1/1973 | Coulter et al. | 324/71.1 |
| 3,946,239 | 3/1976 | Salzman et al. | 250/461 B |
| 3,975,104 | 8/1976 | Munk | 356/246 |
| 3,989,381 | 11/1976 | Fulwyler | 356/39 |
| 4,006,990 | 2/1977 | Munk | 356/246 |

(List continued on next page.)

FOREIGN PATENT DOCUMENTS

| | | |
|---|---|---|
| 155101 | 2/1989 | Denmark . |
| 0068404 | 1/1983 | European Pat. Off. . |
| 0104661 | 4/1984 | European Pat. Off. . |
| 0127418 | 12/1984 | European Pat. Off. . |
| 0158948 | 10/1985 | European Pat. Off. . |
| 0275409 | 7/1988 | European Pat. Off. . |

(List continued on next page.)

OTHER PUBLICATIONS

Kachel et al., *Fast Imaging in Flow: A Means of Combining Flow-Cytometry and Image Analysis*, J. Histochem. Cytochem., 27(a):335–341 (1979).

Milstein, *Monoclonal Antibodies*, Scientific American, 243:56–64 (1980).

*Primary Examiner*—Vincent P. McGraw
*Assistant Examiner*—La Charles P. Keesee
*Attorney, Agent, or Firm*—Merchant & Gould Smith, Edell, Welter & Schmidt

[57] ABSTRACT

An apparatus and a method for analyzing particles suspended in a liquid are described, which particles are of a type or are prepared so as to emit radiation characteristic of the particles when exposed to radiation. Particular fluorescence-photometrical flow cytometry is described in connection with biological cell populations.

The apparatus comprises an elongated flow area in the shape of a channel provided in a cuvette comprising a first body member having a planar facial surface and a second body member having a planar facial surface. The first and the second body members are adapted to be moved relative to one another between a first position, in which the planar facial surfaces are in fluid-tight contact with one another, and a second position, in which the planar facial surfaces are spaced apart. At least one of the planar facial surfaces of one of the body members is provided with an elongated groove. In the first position, the first and second body members together define the cuvette in which the elongated flow area is defined by the elongated groove constituting a capillary passage. An inlet for feeding the liquid to the elongated flow area is provided in one of the body members and an outlet for discharging the liquid from the elongated flow area is provided in the very same or in the other body member. At least one of the body members is transparent to light to which the particles are exposed and further transparent to the radiation emitted by the particles. Two electrodes are further described for carrying out an election of particles suspended in the liquid by means of a measurement of the electrical conductivity of the fluid, which particles are of a specific size for subsequent registration of fluorescence when exposed to radiation.

40 Claims, 12 Drawing Sheets

U.S. PATENT DOCUMENTS

| | | | |
|---|---|---|---|
| 4,510,438 | 4/1985 | Aver | 356/335 |
| 4,521,729 | 6/1985 | Kiesewetter et al. | 324/71.1 |
| 4,565,448 | 1/1986 | Abbott et al. | 356/336 |
| 4,571,078 | 2/1986 | Capps, II | 356/246 |
| 4,643,570 | 2/1987 | Machler et al. | 356/246 |
| 4,823,168 | 4/1989 | Kamahori et al. | 356/246 |
| 4,927,265 | 5/1990 | Brownlee | 356/72 |
| 5,030,002 | 7/1991 | North, Jr. | 356/336 |
| 5,106,187 | 4/1992 | Bezanson | 356/337 |

FOREIGN PATENT DOCUMENTS

| | | |
|---|---|---|
| 0279000 | 8/1988 | European Pat. Off. . |
| 0288029 | 10/1988 | European Pat. Off. . |
| 1673279 | 8/1974 | Fed. Rep. of Germany . |
| 2344427 | 4/1975 | Fed. Rep. of Germany . |
| 2462063 | 11/1975 | Fed. Rep. of Germany . |
| 2721676 | 11/1978 | Fed. Rep. of Germany . |
| 2750447 | 5/1979 | Fed. Rep. of Germany . |
| 2848238 | 5/1979 | Fed. Rep. of Germany . |
| 3033618 | 4/1981 | Fed. Rep. of Germany . |
| 2943116 | 6/1981 | Fed. Rep. of Germany . |
| 3442910 | 5/1986 | Fed. Rep. of Germany . |
| 3530689 | 3/1987 | Fed. Rep. of Germany . |
| 3705876 | 4/1988 | Fed. Rep. of Germany . |
| 3737023 | 7/1988 | Fed. Rep. of Germany . |
| 156916 | 9/1987 | Norway . |
| WO87/00282 | 1/1987 | PCT Int'l Appl. . |
| 8205032-9 | 9/1983 | Sweden . |
| 2116707 | 9/1983 | United Kingdom . |

APPARATUS AND METHOD FOR ANALYZING PARTICLES SUSPENDED IN A LIQUID

The present invention relates to an apparatus and a method for analyzing particles suspended in a fluid medium or liquid, which particles emit radiation characteristic of the particles when exposed to radiation.

The invention relates particularly to analyzing biological cells by means of flow cytometry, more particularly to flow cytometrically analyzing biological cells which are labelled with a fluorescent antibody or which are anti-fluorescent.

In order to provide a better understanding of the fields of application of the invention a brief description is firstly to be given of the biological background of quantitatively measuring biologically relevant parameters of cell populations.

Several cells, both circulating and "fixed" cells, have on their superficial structure so-called antigenic determinants which are specific to the cells in question. Moreover, a number of antigenic determinants are common to different cells, which antigenic determinants may be used as the basis for a general classification.

According to a method well-known within the art and comprising immunizing animals used for experimentation and isolating antibodies present in serum followed by suitably absorbing procedures, it is possible to obtain antibodies which by high specificity are bound to the above-mentioned specific and common determinants. Since the mid-seventies it has been possible to obtain monoclonal antibodies which are further well-defined as they are considered to constitute a homogeneously molecular population. The development of this kind of monoclonal antibodies is very rapid and today there is access to monoclonal antibodies that react with e.g. most human blood cells and their respective subgroups. Furthermore, antibodies capable of reacting specifically with different cancer cells have been cloned.

Antibodies of both of the above-mentioned types may be used for fluorescent-microscopically analyzing cells after conjugation with a Suitable fluorochrome, particularly of the type having green and red fluorescence, e.g. FITC (fluorescein isothiocyanate) and TRITC (trimethyl rhodamine isothiocyanate), respectively. It is known to employ suitable filter combinations in fluorescence microscopes for visualizing the bond of two different antibodies ("green" and "red", respectively) to biological cells simultaneously. Other fluorescent tests may be applied for visualizing and quantifiying cellular components. Thus, ribonucleic acids are detectable by the binding to acridine orange, ethidine bromide or other DNA/RNA-binding colouring agents. Intracellular enzymes may be demonstrated after their reaction with substrate analogues, the cleavage of which results in the formation of a fluorescent product (fluorescein diacetate, methyl umbelly furones). Furthermore, several cells posses specific receptors capable of binding ligands. These ligands are often involved in intercellular recognition and control operations. Fluorescence-labelled ligands (or ligand analogues) may be used for detecting receptors of this type. Finally, several bacteria and algae posses auto-fluorescent properties.

The use of fluorescence spectrophotometry is particularly relevant in connection with the examination of subgroups of the type of cells which can only be distinguished from one another by means of superficial markers which are visualized by means of antibodies. In this field, much attention has been payed to the examination of lymphocytes of peripheral blood. These lymphocyes are dividable into T and B lymphocytes which cannot be separated from one another on the basis of morphological criterions, but on the basis of functional and antigenic differences. Subsequent to antigenic stimulation, the B cells can produce antibodies. These antibodies are exposed on the surface of the B cells and can be utilized for classification by the use of anti-antibodies. The T cells fulfil a number of different functions, both in the control of the immune apparatus and in the direct execution of the cellular immunity. Similarly, the T cells can be divided into a number of subgroups by monoclonal antibodies. Consequently, the examination of the distribution on the various subgroups is relevant in all instances involving the function of the immune apparatus in the broadest sense. The abovementioned subgroups partly overlap one another. Consequently, it is important to be able to examine two or more surface determinants at the same time, i.e. individual stimulus and detection of two or more fluorochromes as indicated above.

Conditions where these kinds of examinations are of interest are among others conditions of immune deficiency, autoimmune diseases, leucemia and other malignant diseases.

For analyzing cell populations of the above-mentioned and corresponding conditions, the presently commercially available apparatuses are very complicated and expensive, and they are generally based upon a general principle according to which the fluid medium is passed through a small aperture, in which fluid medium fluorescence-labelled biological particles to be analyzed are suspended, around which aperture a carrier fluid is passing so as to produce a carrier-fluid stabilized laminar flow of the fluid medium in which the particles to be analyzed are suspended. The laminar flow is exposed to radiation in a direction defining an angle relative to the direction of flow of the fluid medium by means of a constantly luminous laser lamp, such as an argon laser, and the fluorescence of all the particles fluorescent when influenced by the monochromic light of the laser is picked-up, e.g. at an angle of 90°, and is analysed. In order to obtain sufficient light energy by the prior art apparatuses, it is necessary to use a laser lamp, which inherently renders the apparatuses very expensive. Furthermore, a system based upon the utilization of the above-described laminar flow is not ideal since the fluid medium in which the biological particles are suspended must be discharged from an admission pipe having a small aperture, in order to be conveyed as the described laminar flow, which small aperture tends to block. Moreover, the analysis normally comprises all fluorescent particles, whether they have a size corresponding to that of the cells to be analyzed or not. Apparatuses of the type mentioned above have been disclosed in the patent literature, cf. e.g. U.S. Pat. Nos. 3,946,239, 3,989,381, SE patent no. 429 479, EP patent no. 0 068 404 and EP patent no. 0 279 000.

Furthermore it is known within the art to count particles suspended in a liquid in accordance with the so-called the Coulter principle, which is based upon the generation of a constant electrical field or a constant voltage across an aperture, through which the fluid medium in which particles are suspended is passed. When a particle passes through the aperture, a change of the conductivity of the fluid may be registered by a current measurement, indicating that a particle has passed through the aperture. This measurement may also to some extent be indicating of the magnitude or size of the particle, the measurement is, however, subjected to considerable inaccuracy, among other things determined by whether the particle passes through the center of the aperture or whether the particle passes through the aperture at a position closer to the periphery of the aperture. The patent literature regarding analyzing particles on the basis of the Coulter principle is very extensive and as examples is hereby referred to basic U.S. Pat. No. 2,656,508 by W. H. Coulter, DE-OS 23 44 427, U.S. Pat. No. 3,714,565, and DE-AS 16 73 279. The conventional particle analysis based on the Coulter-principle is not suitable for the above-mentioned prior art apparatuses based upon a laminar flow and laser light, among other things because it is very difficult to implement a laminar flow of this kind provided the liquid flow is to pass through a small aperture. The above-mentioned EP patent no. 0 068 404 discloses an example of the application of two electrodes in connection with a laminar flow, however, the electric field established by the generation of a voltage across the two electrodes is not well-defined and does not offer the possibility of an accurate counting nor a volume fluid determination.

Cuvettes having a flow area in the form of a capillary passage are well-known within the art and may be utilized for measuring colour absorption of fluids which do not contain particles that may block the capillary passage. An example of this type of cuvette is disclosed in EP patent no. 0 158 948, which discloses a flow cuvette assembled from two cuvette body halves, in which the even surfaces, which are positioned adjacent one another when the cuvette is assembled, are provided with grooves of the surfaces of the joining surfaces and comprise a flat chamber arranged in a central part. This prior art cuvette is intended for volumes of the order of nanoliters and may, particularly due to the small dimensions of the analysis chamber in one direction, only be utilized for analyzing particlefree fluids, as is clearly stated in said patent. The two-part cuvette is secured by means of a spring device, and by release of the spring device the two cuvette body halves will drop randomly so that they must be positioned manually when the cuvette is to be reassembled. From U.S. Pat. No. 4,823,168, a flow cell is known comprising a small flow passage provided by a permanent joining of the two cuvette body halves having grooves on their joining surfaces. This prior art flow cell is solely intended for photometrically analyzing liquids which do not contain particles that may block the flow passage, and the two flow cell body halves are not adapted to be separated once assembled. The photometric measurement is established by submitting light through a flow passage in a direction coincident with the flow direction of the liquid.

The present invention provides an apparatus and a method suitable for analyzing fluorescence-labelled or autofluorescent particles of cells suspended in a liquid, which apparatus, however, does not suffer from the disadvantages of the above-mentioned prior art apparatuses, which rely on an expensive laser lamp, and by which the fluid medium must be fed from a feeding pipe having a small aperture, from which the fluid medium is supported by an exterior carrier fluid. Accordingly, the invention provides the possibility of utilizing a low-energy light source, e.g. a iodine quartz photoflood lamp of e.g. only 100 W, or a flash lamp, e.g. a xenon flash lamp.

According to an embodiment of the apparatus and the method according to the invention, it is possible to combine spectrophotometrically fluorescence-analyzing technique and counting and a determination of the sizes of the particles to be analyzed, which counting and determination of the sizes of the particles are based on a modified Coulter-principle.

According to a further embodiment of the apparatus and the method according to the invention, it is possible, when analyzing, to pass a fluid medium containing a fluid medium in which biological particles are suspended through a passage having the dimensions of a capillary passage providing a highly reduced risk of blocking the passage and providing a simple cleaning capability, in the event blocking occurs. When analyzing, the utilization of a passage having small cross-sectional dimensions provides a particular advantage in that the particles to be analyzed sequentially arrive at the measuring area individually, which is not possible by the aforementioned laminar flow technique comprising a carrier fluid.

According to a further embodiment of the apparatus and the method according to the invention, the particles arrive at the measuring area as close to one another as possible without coincidence, i.e. coincidence of measurements from more particles, thus increasing the measuring rate as compared to the prior art technique.

According to an embodiment of the apparatus and the method according to the invention, the liquid containing the particles to be analyzed pass through the flow system as a laminar flow of constant rate without utilizing a carrier fluid.

Further advantages, aspects, features and objects of the present invention will appear from the description below.

The invention is to be explained in greater details below, particularly relating to flow-cytometrically analyzing biological cells which are flourescent having a characteristic fluorescent radiation when subjected to illumination, it is, however, to be understood that the invention is also appliable in connection with a so-called light scatter or other analyzing methods based upon incident radiation, by which the relevant particles emit radiation characteristic of these particles.

Moreover, the invention will be explained particularly in relation to a fluid medium in which biological cells to be analyzed are suspended, which fluid medium is passed through a passage having cross-sectional dimensions adapted to the size of the cells, and which fluid medium is exposed to light for illuminating the cells individually. Consequently, the existence of an elongated flow area having the dimensions of a capillary passage is mandatory, however, causing problems as regards blocking of the passage. The principles and the techniques according to the invention are considered generally applicable as they may be utilized for substantially bigger, nonbiological particles, provided that the particles are capable of emitting a characteristic radiation when exposed to radiation.

According to the preferred embodiments of the apparatus and the method according to the present invention, which embodiments particularly tel ate to spectrophotometrically fluorescence-analyzing biological cells, a unique technique is provided, which is well-suited for the aforesaid analyzing of particular cell populations comprising subgroups of cell types which can only be distinguished from one another by means of superficial markers exposed by antibodies.

In a first aspect, an apparatus according to the invention is provided comprising:

a cuvette, in which an elongated flow area having the shape of a passage is provided for guiding the fluid medium in which the particles are suspended in a first direction, means for feeding the fluid medium in which particles are suspended to the elongated flow area, means for discharging the fluid medium in which particles are suspended from the elongated flow area, means for exposing the fluid medium in which particles are suspended to radiation in a second direction defining an angle relative to the first direction, in which the fluid medium is guided through the elongated flow area, means for picking-up at least part of the radiation characteristic of the particles and emitted by the particles when exposed to radiation, said elongated flow area having the shape of a passage provided in a cuvette comprising a first body member having a planar facial surface and a second body member having a planar facial surface, said first and second body members being movable relative to one another between a first position, in which the planar facial surfaces are positioned closely adjoining one another in a fluid-tight manner, and a second position, in which the planar facial surfaces are positioned spaced apart, at least the facial surface of the first body member being provided with an elongated groove defining together with the adjoining facial surface of the second body member the elongated flow area constituting the passage, when the body members are in the first position, the means for feeding the fluid medium in which particles are suspended to the elongated flow area comprising an inlet provided in one of the body members and extending from the exterior of the cuvette to an inlet aperture of the passage, the means for discharging the fluid medium in which particles are suspended comprising an outlet provided in one of the body members and extending from an outlet aperture of the passage to the exterior of the cuvette, and at least one of the body members being transparent to the radiation to which the fluid medium is exposed and to the radiation emitted by the particles.

According to the present invention, the elongated flow area is provided by the assembling of the cuvette from two component body members, which are adapted to be positioned closely adjoining one another through the respective planar facial surfaces, and in at least one of which the elongated groove is defined, e.g. provided by a milling operation. The elongated groove is preferably only provided in one of the facial surfaces. Consequently, the elongated flow area is defined by the groove and the adjoining facial surface of the second body member. It is, however, within the scope of the invention to provide opposite and cooperating grooves in the planar facial surfaces of both body members. However, an embodiment in which two cooperation grooves are provided has been found unsuitable due to the possible complications likely to occur when assembling the two body members as the grooves of both body members are to be positioned extremely accurately relative to one another.

The two body members are adapted to be moved between a first position, in which the planar facial surfaces are positioned adjacent one another in a fluid-tight manner, and a second position, in which the planar facial surfaces are positioned spaced apart. Positioning the body members in the first position so as to avoid the leakage of the fluid medium from the cuvette, the two planar facial surfaces are preferably polished smoothly, and according to a preferred embodiment of the apparatus according to the invention, a spring loading means is provided, which actuates at least one of the body members by a spring force perpendicular to the facial surface of the opposite body member, which spring loading means further allows a tilting or a change of the angle of the body member which is loaded by the spring loading means.

In the first position, in which the planar facial surfaces of the body members are arranged adjacent one another, the analysis is conducted in a manner to be described in greater details below. Having finished the analysis, the planar facial surfaces are moved relative to one another to the second position, in which the planar facial surfaces and further the feeding and discharging means are cleaned, rinsed or washed, as will be explained below. The planar facial surfaces of the body members are also cleaned, rinsed or washed, provided the elongated flow area is blocked unintendedly.

According to the preferred embodiment of the apparatus according to the invention, the first and second body members are movable relative to one another by parallelly displacing at least one of the two body members in a direction perpendicular to the planar facial surfaces of the body members.

According to the preferred embodiment of the apparatus according to the invention, a stop means is provided, which stop means receives the spring loaded body member, when the body members are moved to the second position so as to maintain the springloaded body member in a well-defined position, in which the facial surface of the spring-loaded body member is maintained substantially parallel with the opposite facial surface.

The means for the feeding of the fluid medium in which particles are suspended is preferably constituted by a feeding channel or passage, which extends from the exterior relative to the cuvette to the inlet aperture of the elongated flow area. The means for discharging the fluid medium in which particles are suspended preferably comprises a discharge channel or passage provided in the same or in the other body member, which discharge passage extends from the outlet aperture of the elongated flow area to the exterior relative to the cuvette. As may be understood, the feeding passage and the discharge passage may be provided in different body members. The feeding passage and the discharge passage are, however, preferably provided in one of the body members exclusively and constituted by respective bores extending between an outer surface of the body member in question and the elongated flow area.

The bores are preferably provided in the first body member, the facial surface of which is provided with the elongated groove. Provided the feeding passage and the discharge passage are provided in the second body member having no elongated groove, it is extremely difficult to ensure that these passages will lead precisely into the elongated flow area, when the body members have been opened and reclosed, and will also cause optical problems as will be understood from the description below.

In order to allow the particles suspended in the liquid to be exposed to radiation, at least one of the body members is transparent to the radiation to which the particles are exposed, and at least one of the body members is transparent to the radiation emitted by the particles. Consequently, at least one of the body members is preferably transparent and is preferably made from quartz glass.

According to the preferred embodiment of the apparatus according to the invention, the first body member, i.e. the body member the facial surface of which is provided with the elongated groove and the body member preferably comprising the feeding and discharge passages needs not to be transparent, but is preferably also made from quartz glass.

In the preferred embodiment of the apparatus according to the invention, the elongated flow area defined between the two body members of the cuvette constitutes a capillary passage as explained above and preferably has the shape of a geometrical section of a rectilinear cylinder having a circular cross-section of a radius of curvature not exceeding 1 mm, preferably not exceeding 100 $\mu$m, most preferably 50 $\mu$m, and having a depth not exceeding 1 mm, preferably not exceeding 100 $\mu$m, and most preferably 30–35 $\mu$m. This dimension of the passage is suitable for biological cells having a diameter of the order of 8–15 $\mu$m, which is the normal size of some lymphocytes. The above-mentioned dimensions of the elongated flow area have been defined on the basis that the particles are to arrive at the measuring area individually whenever possible, and the cross-sectional dimension of the elongated flow area is consequently determined in consideration of the particles to be analyzed. It is not required that the particles pass individually and sequentially through the feeding passage. However, in order to minimize problems regarding blocking of the feeding passage, the feeding passage preferably has dimensions that are far larger than those of the elongated flow area. Experiments have, however, revealed that the bore constituting the feeding passage should preferably not be larger than e.g. 3 mm, since larger dimensions make it difficult to ensure that the particles arrive at the elongated flow area homogeneously. Provided the diameter of the feeding passage is less than 3 mm, a capillary passage effect occurs and a risk of blocking the feeding passage exists.

In an alternative or additional embodiment of the apparatus according to the invention, the problem of eliminating blocking of the feeding passage is solved by means of an agitating means. In accordance with this embodiment of the apparatus according to the invention, the feeding passage is constituted by a bore of a diameter not exceeding 3 mm, preferably not exceeding 2 mm, particularly of the order of 1 mm, extending through one of the body members, preferably the first body member, through which bore a flexible wire body extends, which is rotatable relative to its longitudinal axis, one end portion of which wire body is connected to a wire rotating means, and the opposite end portion of which wire body extends into the elongated flow area. The wire body preferably contacts the facial surface of the elongated flow area channel opposite to the inlet aperture of the elongated flow area.

The flexible wire body may have a non-circular cross-section, particularly a polygonal, particularly a tetragonal or triangular cross section, preferably a square cross section having a lateral dimension of the order of 0.2–0.5 mm, particularly of 0.3 mm when the bore constituting the feeding passage has a diameter of the order of 1 mm.

Alternatively, the flexible wire body may have a circular cross section of a cross-sectional dimension of 0.2–0.5 mm, and particularly of 0.3 mm. This wire body has been found to provide an advantageous agitation, and it is distinguished by providing a uniform movement, which is less liable to cause mechanical or electrical disturbances or noise than a polygonal-shaped wire body.

The flexible wire body is preferably made from a plastic material which only swells insignificantly in water under the prevailing conditions, e.g. nylon, polypropylene, polycarbonate or Teflon.

This type of agitating means comprising a wire, which is rotatable relative to its longitudinal axis, and which is arranged in the feeding passage constituted by a bore of the above-mentioned dimensions, has not been disclosed previously within the prior art constituting an agitating device for agitating particles suspended in a liquid. Surprisingly this wire body has proved capable of avoiding any agglomeration of biological cells, capable of avoiding that the particles stick to the the surface of the passage and capable of ensuring that the particles are distributed homogenously at the inlet aperture of the elongated flow area. This effect is improved when the wire body has a non-circular cross section, particularly a polygonal, preferably a tetragonal or triangular cross section, most preferably a square cross section of the above-mentioned dimensions. When rotation about its longitudinal axis, the wire body more or less assumes the shape of a spiral. The wire body may rotate clockwise or counter-clockwise or alternating in both directions.

By providing the wire body projecting into the capillary passage constituted by the elongated flow area, and preferably contacting the facial surface opposite to the the inlet aperture of the capillary passage, it is possible to avoid a blocking of the capillary passage. It is to be understood that the end section of the wire body which projects into the capillary passage normally has a cross section of a substantially larger dimension than that of the capillary passage. The wire rotating means for the flexible wire body may be a magnet agitator as will be explained in greater details below, from which magnet agitator the wire suspends through gravitational force.

For exposing the particles suspended in the liquid so as to cause the particles to emit radiation characteristic of the particles, a laser lamp, e.g. an argon laser, may be applied, the radiation of which laser lamp is directed to the elongated flow area at a predetermined area thereof. As it is indicated above, the application of a laser lamp is, however, not preferred, and the provision of the capillary passage constituted by the elongated flow area according to the teachings of the present invention, in which area the particles preferably pass individually, in a unique way renders it possible to employ a radiation source having a relatively low energy consumption, such as an incandescent lamp, and preferably a halide lamp, e.g. a iodine quartz lamp of a rating of e.g. only 100 watt. Also a flash lamp may be used, e.g. a xenon flash lamp. By the utilization of this kind of radiation source, the apparatus is provided with an optical system as explained in greater details below, which system renders it possible to focus the radiation to which the particles are exposed on a predetermined subsection and a specific area of the elongated flow area. By this kind of radiation, whether it is provided by means of a laser or by means of a light source having essentially lower energy, fluorescence-labelled particles or auto-fluorescent particles are stimulated and emit characteristic fluorescence radiation. In the present context, the subsection at which the particles are stimulated by radiation is called the focusing area, whether in relation to optically focussed light or in relation to parallel incident rays emitted from a laser lamp. In view of optically focussed light, the last part of the radiation operation for focusing on a predetermined subarea of the particles suspended in a liquid is preferably, according to the invention, constituted by an objective lens having a planar surface, which in a light-transmitting relationship is fixed to a surface of one of the body members, which surface is parallel with the planar facial surfaces of the body members.

In order to obtain a maximum detection of the radiation emitted by the particles, a reflecting surface for reflecting radiation emitted by the particles, suspended in the fluid medium or liquid and exposed to radiation, is provided in the cuvette, at least behind the focusing area, according to the preferred embodiment of the apparatus according to the invention. According to the invention, the reflecting surface is preferably provided in the elongated flow area constituted by the capillary passage at the area which is located behind the focusing area as seen in the direction of transmission of the radiation to which the particles are exposed. The reflecting surface is preferably constituted by a polished surface of a metal member or body, which is flush-mounted within the capillary passage.

An apparatus as described basically provides a substantial progress in relation to the previously mentioned, commercially available, prior art apparatuses comprising centrally fed particles suspended in a liquid, which particles are supported by a laminar liquid flow, and which fluorescence-labelled particles are stimulated by means of a laser lamp. It is particularly to be pointed out that, by the apparatus according to the invention to be described below, it is possible to utilize a low-energy light source in connection with a capillary passage and at the same time to solve the blocking problems to be expected.

According to a further aspect of the present invention, a more elaborated apparatus is provided, which in addition to the optical measurement allows electronical measurement based upon a modified Coulter principle. By means of this principle, which is to be explained in greater details below, it is possible to determine the size of the particles suspended in the liquid before the arrival of the particles at the focusing area, and consequently possible to expose specific particles and register fluorescence of specific particles, which fulfil specific and predetermined criterions as to their size. E.g. a blood sample contains many particles of varying sizes apart from lymphocytes of a magnitude of the order of 8-15 $\mu$m, which other particles are irrelevant in view of an analysis for determining subpopulations of lymphocytes. In accordance with this further aspect of the present invention, which aspect is to be explained in greater details below, and which is based upon a modified Coulter principle, it is possible to detect the existence of one particle of the relevant size of e.g. 8-15 $\mu$m among a plurality of different particles passing through the capillary passage. Having determinated this type of particle and after exposure of the particle to the radiation, the particle emits fluorescence radiation characteristic of the particle shortly after its arrival at the focusing area, provided a specifically fluorescence-labelled antibody is bound to the antigenic determinants of the particle. Particles having outer dimensions outside the relevant dimensional range or particles having outer dimensions within the relevant dimensional range, which last-mentioned particles, however, are non-fluorescent, are not detected. The employment of the flash, as discussed above, is particularly interesting in this context, as the employment of a flash for generating the radiation or light renders it possible to activate the flash for emitting the radiation or light to which the particles are exposed at the specific time at which the particle which has been detected by means of the electrical field and has been evaluated as a particle having an outer dimension within the relevant dimensional range is passing through the specific area or the focusing area of the elongated flow area, in which specific area or focusing area the particle is exposed to the radiation or the light generated by the flash.

According to the above-mentioned, further aspect of the present invention constituting a more elaborated apparatus according to the invention, at least two electrodes for generating an electric field through which the fluid medium is passed when guided through the elongated flow area are provided. By arranging the electrodes in an appropriate manner, a measurement of the conductivity of the elongated flow area is accomplished in a manner known per-se in accordance with the so-called Coulter principle. However, according to the teaching of the present invention in accordance with this further aspect of the present invention, it is rendered possible to detect the passing of a particle of a specific outer dimension through the elongated flow area and further, by exposing the particle to the radiation generated by the means for exposing the fluid medium, the existence of a fluorescent particle is registered or detected. According to the preferred embodiment of the apparatus according to the present invention and according to the above-described, further aspect of the present invention, the electrodes are embedded within the first or second body member providing exposed electrode surfaces at the elongated flow area. Preferably, the electrodes are arranged in succession relative to the first direction, in which the fluid medium is guided through the elongated flow area, for generating the electrical field having lines of flux extending at a part of said elongated flow area substantially homogenously and substantially parallel with the first direction.

According to the Coulter principle well-known in the art per-se, the electrical impedance across the electrodes is detected, e.g. by supplying a constant voltage or a constant current to the electrodes and by measuring the current or voltage thus generated, respectively, or in accordance with a combination technique involving the generation of a combined voltage and current signal and the detection of a combined voltage and current signal. Provided the particles are passing through the elongated flow area individually, which is preferably accomplished in accordance with the teaching of the present invention, as will be disclosed in greater details below, an electrical signal is generated across the electrodes, which electrical signal constitutes a measurement of the electrical conductivity or impedance of the medium to which the electrical field is supplied, which electrical signal is directly correlated with the volume of the particle and consequently the outer dimension or size of the particle to which the electrical field is presented. Consequently, the electrical signal is easily convertible into a measurement representing the volume or outer dimension of the particle in question.

Provided the electrodes are embedded within the first or the second body member and are arranged in succession relative to the first direction, in which the fluid medium is guided through the elongated flow area, and further provided the elongated flow area constitutes a capillary passage, the optimum spacing between the electrodes is determined by and related to the dimension of the capillary passage and is mandatory to the provision of the homogenous and substantially parallel electrical field within the part of the elongated flow area in which part the electrical field is generated. According to the present invention, the electrodes are preferably spaced apart at the elongated flow area defining a minimum spacing of the order of 0.05–0.3 mm, such as 0.08–0.2 mm, preferably approximately 0.08 mm. The above figures are particularly relevant provided the capillary passage constituted by the elongated flow area has the shape of a geometrical section of a rectilinear cylinder having a circular cross section of radius of curvature less than 1 mm, preferably less than 100 $\mu$m, most preferably approximately 50 $\mu$m. Provided the electrodes are provided in one of the body members of the cuvette exclusively, the electrodes may be embedded within the second body member or alternatively and preferably within the first body member, in which the elongated groove is provided.

As discussed above, the means for exposing the particles to radiation is preferably constituted by a light source generating a continuous light or further preferably generating the light intermittently. The light generated by the light source, which light is generated continuously or alternatively and preferably generated intermittently, is further preferably focused at a specific area of the elongated flow area, by providing e.g. a lens constituting an integral part of the light source, or alternatively or preferably by providing a focusing means constituted by an objective lens, which is arranged in direct optic communication with the cuvette, for focusing the light at the specific area of the elongated flow area at which the particles of the fluid medium passing through the elongated flow area are exposed to the radiation or light thus focused.

According to the above-described, further aspect of the present invention, a light reflecting means is preferably provided for reflecting the radiation emitted by the particles when exposed to the light or radiation from the light source or from the means for exposing the fluid medium to radiation, to the means for picking up the radiation generated by the particles. According to the above-described, preferred embodiment of the apparatus according to the present invention, in which preferred embodiment the electrodes are embedded within one of the body members and define exposed electrode surfaces at the elongated flow area, the light reflecting means is advantageously constituted by one of the exposed electrode surfaces, further preferably constituted by the exposed electrode surface of the electrode which constitutes the downstream electrode of the pair of electrodes arranged in succession relative to the first direction, in which the fluid medium is guided through the elongated flow area.

As will be described in greater details below, the apparatus according to the present invention renders it possible in an extremely elegant and rapid manner to eliminate a blocking of the feeding means and further of the elongated flow area of the cuvette, provided blocking occurs. Furthermore, it is of the utmost importance, as indicated above, to present the particles to the electrical field and further to exposure to the radiation or light individually. For accomplishing an individual presentation of the particles to the electrical field and further to the light or radiation to which the particles or the particle are to be exposed individually, the apparatus further preferably comprises a means for feeding a diluent to the elongated flow area so as to render it possible to add the diluent to the fluid medium present within the elongated flow area. As indicated and discussed above, the particles are to be presented to the electrical field and to the radiation individually and consequently to be guided through the elongated flow area in a spaced apart relationship. The spacing between any two adjacent particles should, however, not be too extreme, as an extreme spacing between any two particles reduces the measuring rate and consequently the capability of the measuring apparatus, as an extreme spacing between any two adjacent particles reduces the rate at which the particles are presented to the electrical field and further to the light or radiation as compared to a smaller spacing between any two adjacent particles.

The provision of the means for feeding the diluent to the elongated flow area renders it possible to control the flow rate of the particles passing through the elongated flow area, preferably by providing means for controlling the supply of the diluent to the elongated flow area. As discussed above, the apparatus preferably comprises a control means, which preferably further is connected to and controls the means for controlling the supply of diluent to the elongated flow area. Thus, provided a control means detects the presence of particles of a concentration within the elongated flow area exceeding a maximum concentration, the control means addresses the means for controlling the supply of the diluent to the elongated flow area for adding the diluent to the elongated flow area and consequently for reducing the concentration of particles within the elongated flow area. The means for feeding the diluent to the elongated flow area is preferably arranged upstreams relative to the electrodes. Furthermore, the control means controlling the means for controlling the supply of the diluent to the elongated flow area may establish the controlling so as to provide a predetermined particle flow rate through the elongated flow area or a predetermined concentration of particles within the elongated flow area, or alternatively so as to present the particles to the exposure means individually and at a rate lower than a predetermined maximum rate, such as a rate of 100 particles per second.

It has further been realized that an optimum analysis and measurement is established provided the fluid medium is guided or passed through the elongated flow area as a laminar flow of a constant rate. Consequently, according to a specific feature and aspect of the present invention, the apparatus further comprises a flow control means for controlling the flow of the fluid medium through the elongated flow area. The flow control means is preferably constituted by a pump connected to the means for discharging the fluid medium from the elongated flow area and generates a substantially constant flow rate of the fluid medium through the elongated flow area.

As indicated above, a particular feature and advantage of the apparatus according to the present invention is the capability of the apparatus of providing an easily and rapidly accomplished elimination of a blocking of the means for feeding the fluid medium to the elongated flow area or of the elongated flow area, provided such blocking occurs. Thus, a blocking is easily eliminated by moving the first and second body members relative to one another towards or to the second position, preferably for at short period of time of the order of 20 ms, by which opening of the cuvette comprising the first and second body member, the fluid medium and the particles suspended therein present in the elongated flow area of the cuvette is expelled from the elongated flow area, by which expelling the blocking is also eliminated.

In order to render it possible to provide an easy rinsing or cleaning of the cuvette, which cleaning is carried out when the body members of the cuvette are in the above-described second position, the apparatus preferably further comprises a rotatable rinsing brush, which is movable relative to the body members across the planar facial surfaces thereof, when the body members are in the second position, for mechanically cleaning the planar facial surfaces of the body members.

The above-described aspect of the present invention, viz. the possibility of controlling the exposure of the particles guided through the elongated flow area of the cuvette in response to the detection of the presence of a particle having an outer dimension or a volume within a specific and relevant dimensional range, is believed to constitute an independent, inventive concept.

The possibility of providing an "on-line" diluent operation, while the fluid medium in which the particles are suspended is guided through the flow area by the introduction of the diluent into the elongated flow area of the cuvette, in order to provide an adequate spacing of the particles that are exposed to radiation or light and further an adequate concentration of particles and an adequate flow rate of the particles guided through the elongated flow area, is also believed to constitute an independent, inventive concept.

The present invention further relates to a method of analyzing particles suspended in a liquid by employing an apparatus according to the present invention and optionally having the above-described features and advantages in accordance with the above-described aspects and embodiments of the apparatus according to the present invention. Thus, according to a further aspect of the present invention, a method of analyzing particles suspended in a liquid is provided by employing an apparatus according to the present invention, which method comprises the following steps:

feeding the fluid medium in which the particles are suspended into the elongated flow area through the means for feeding the fluid medium to the elongated flow area, guiding the fluid medium in the first direction through the elongated flow area of the cuvette, exposing the fluid medium in which the particles are suspended to the radiation in a second direction defining an angle relative to the first direction, picking up at least part of the radiation characteristic of the particles and emitted by the particles when exposed to radiation by means of the means for picking up at least part of the radiation characteristic of the particles and emitted by the particles when exposed to radiation, discharging the fluid from the elongated flow area by means of the means for discharging the fluid medium from the elongated flow area, and in case a blocking of the elongated flow area or of the means for feeding the fluid medium to the elongated flow area occurs, moving the first and second body members to the second position so as to expel the fluid medium from the elongated flow area and further from the means for feeding the fluid medium to the elongated flow area, and thus eliminate the blocking.

The method according to the present invention preferably comprises the above aspects, advantages and features of the specific aspects and embodiments of the apparatus according to the present invention.

Figure 2:
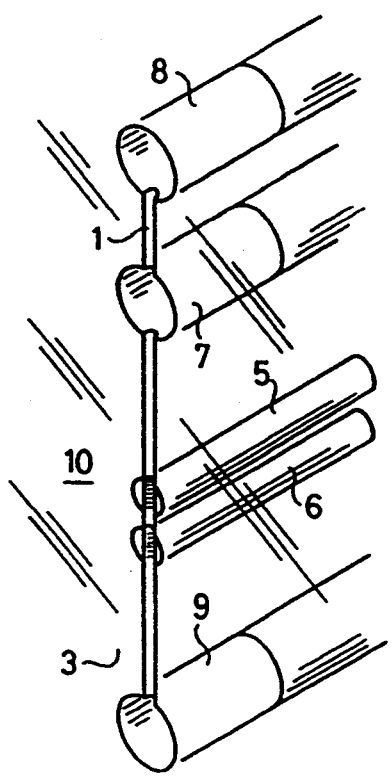
Figure 3:
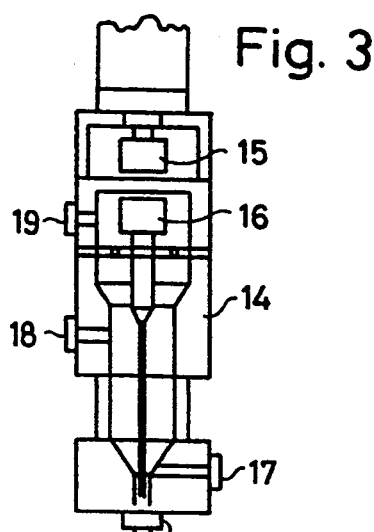
Figure 4:
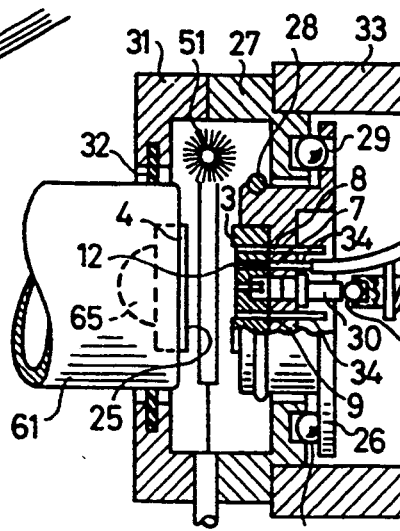
Figure 5:
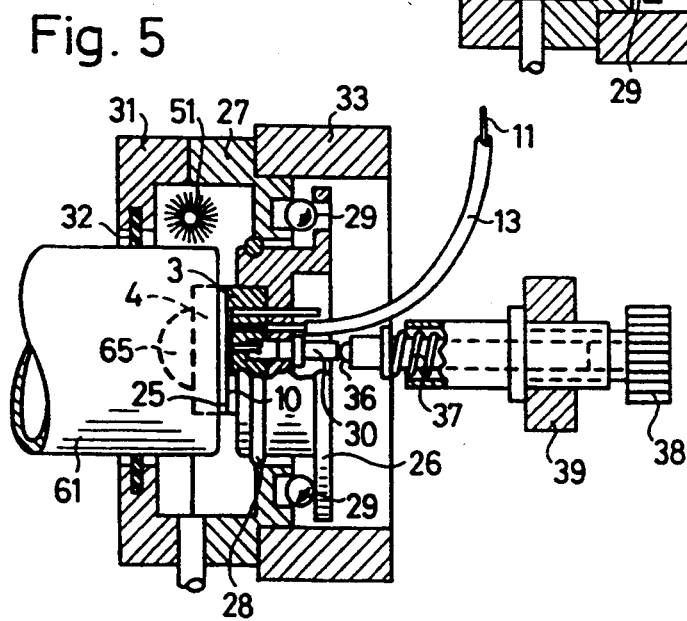
Figure 7:
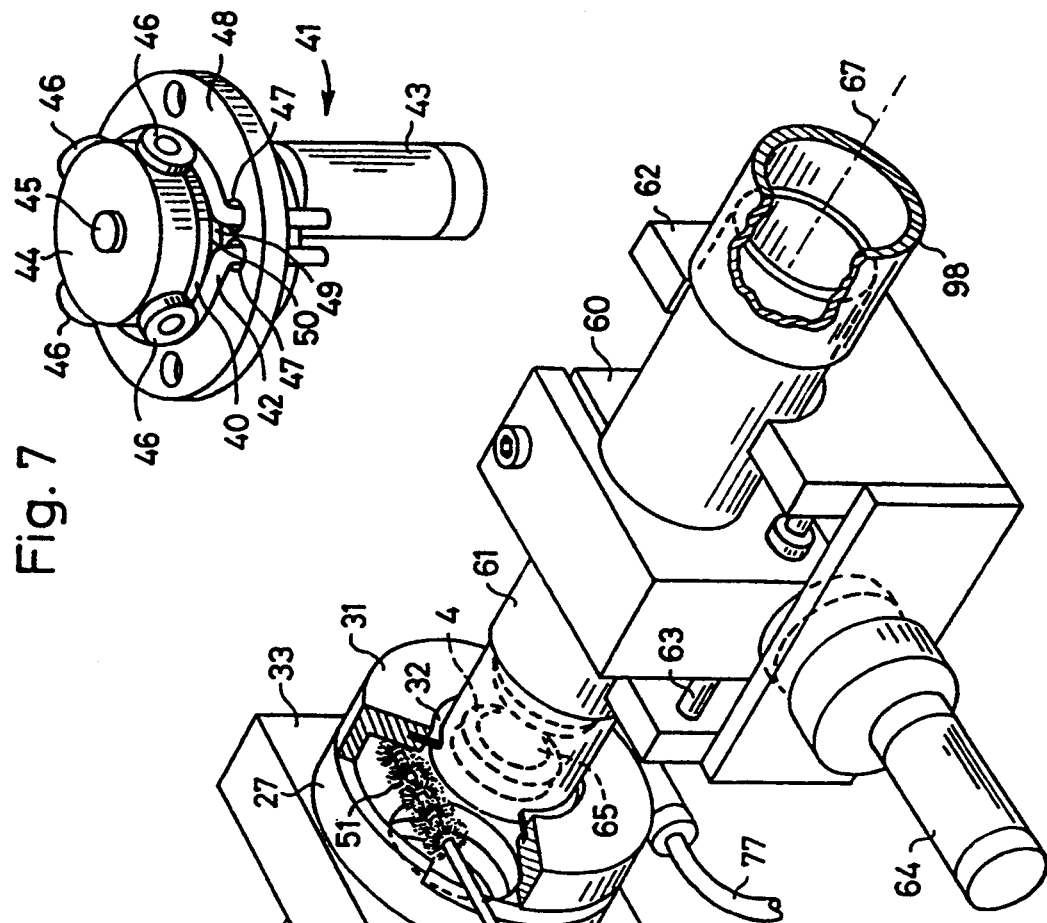
Figure 6:
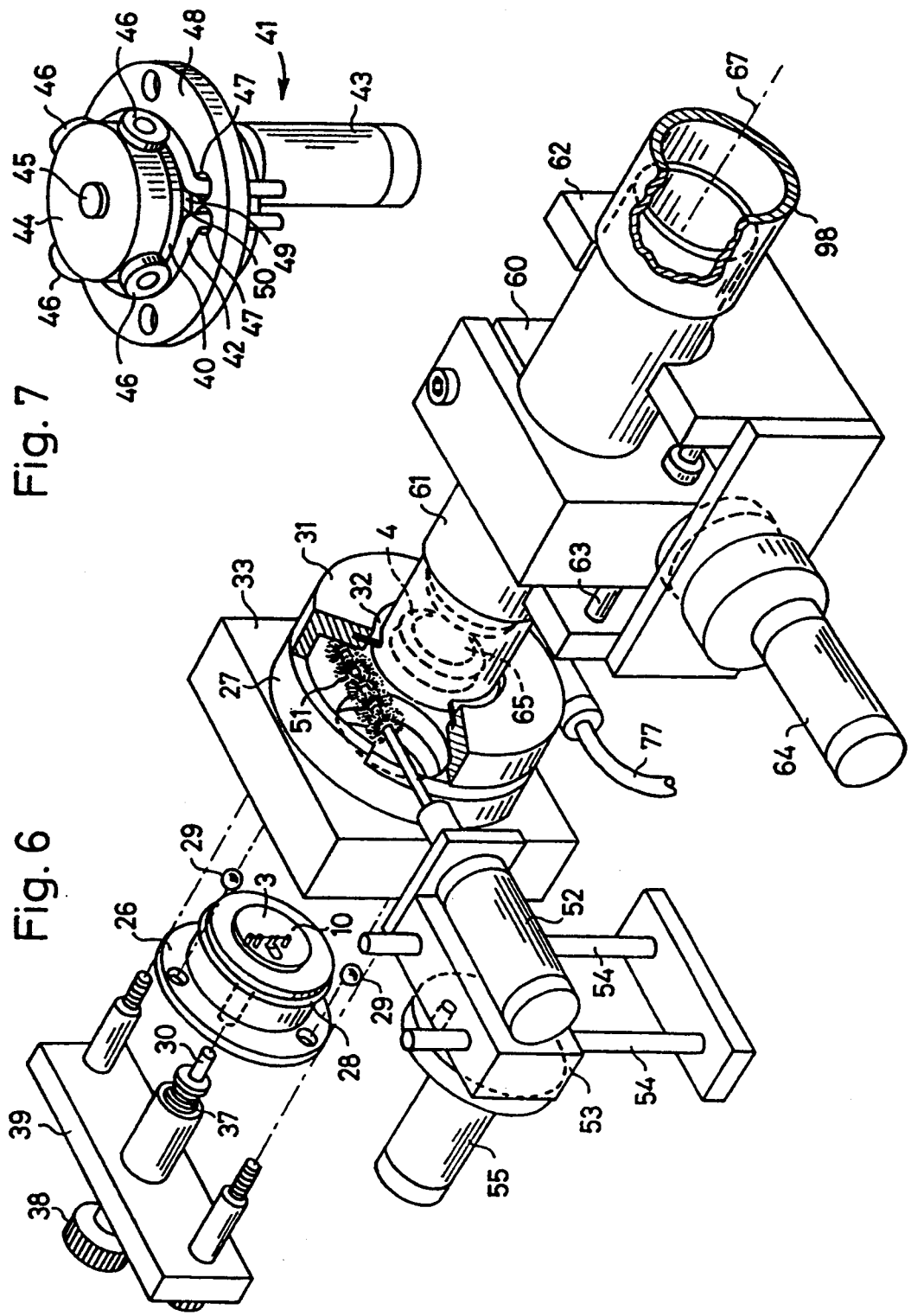
Figure 8:
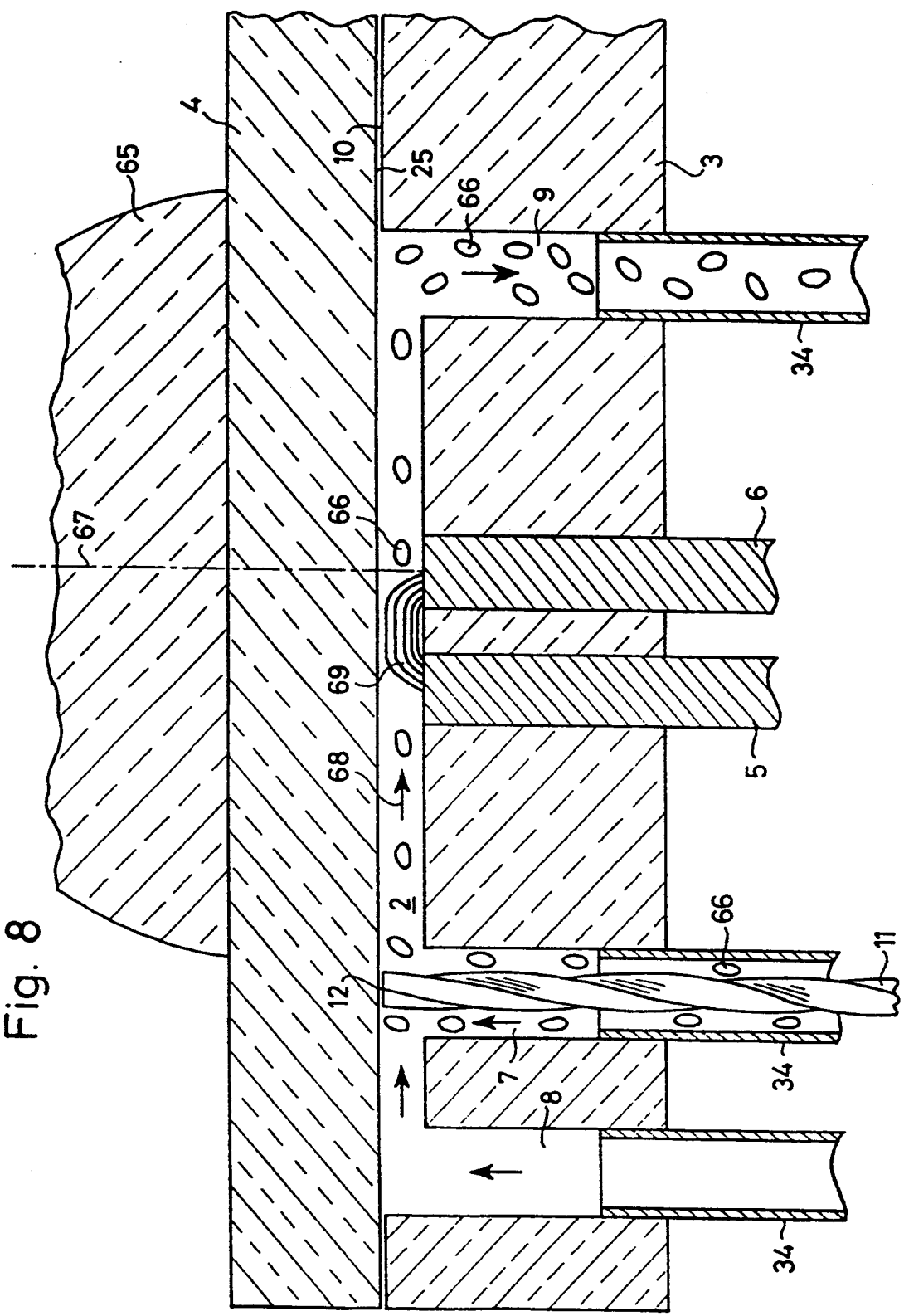
Figure 9:
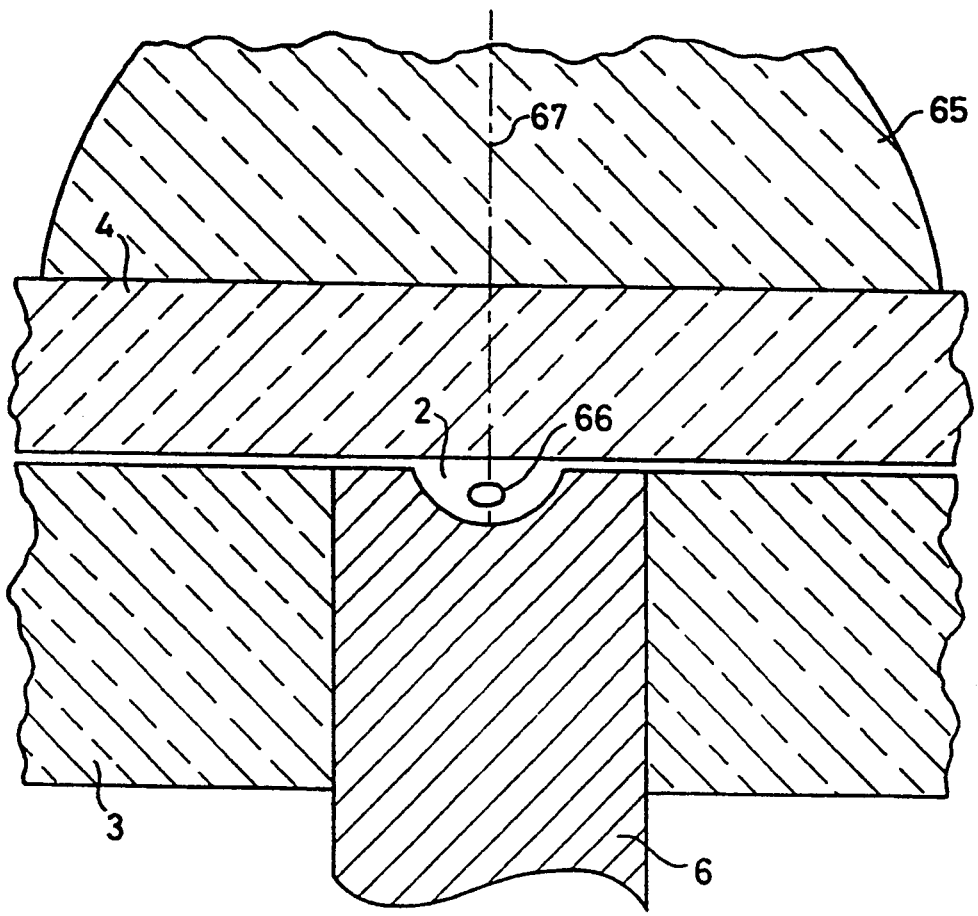
Figure 10:
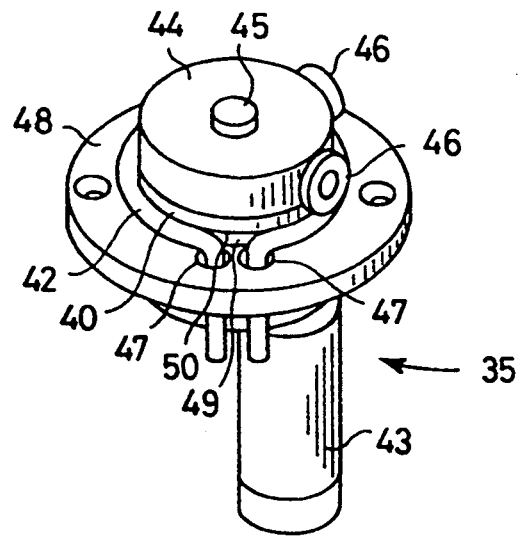
Figure 11:
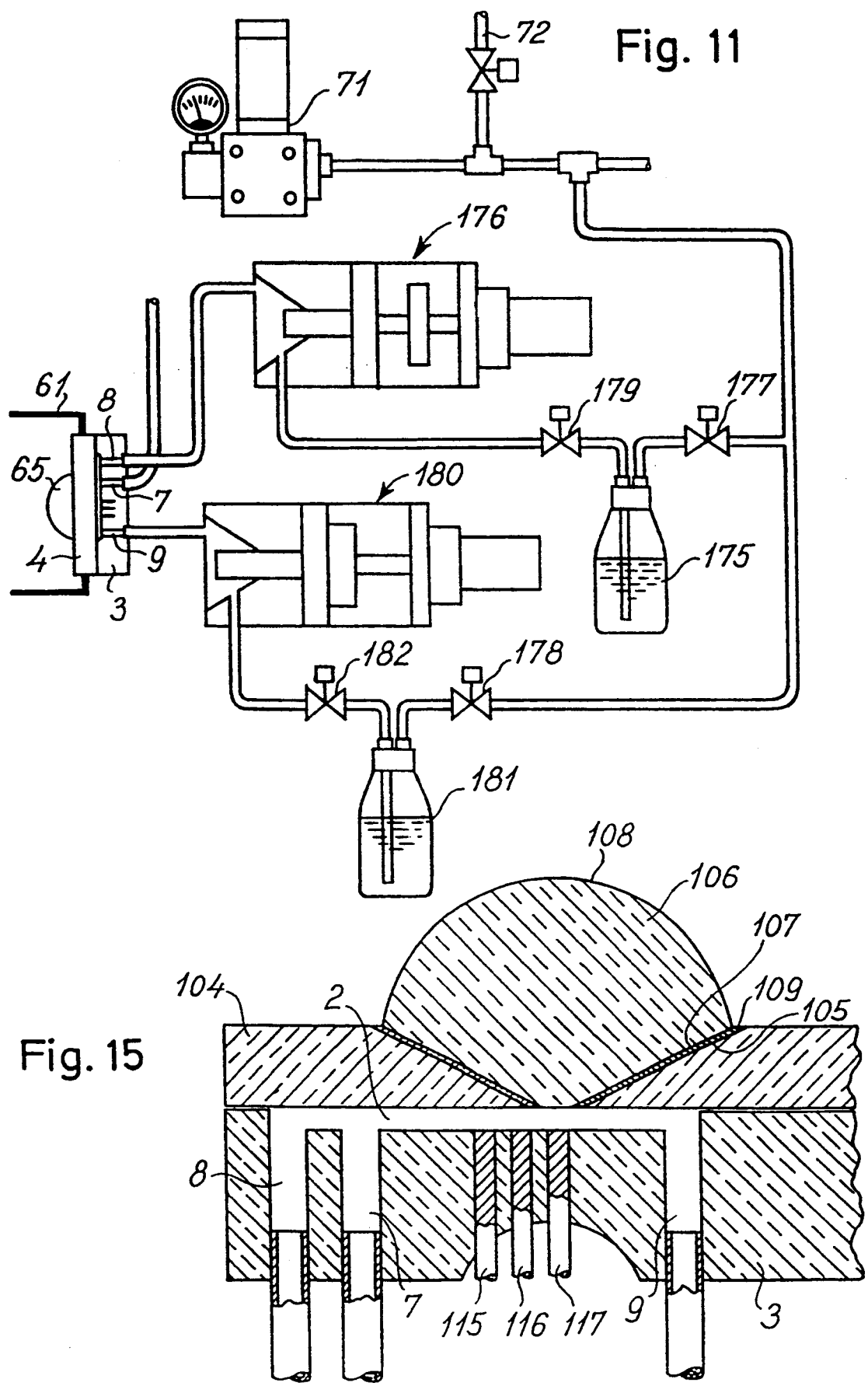
Figure 12:
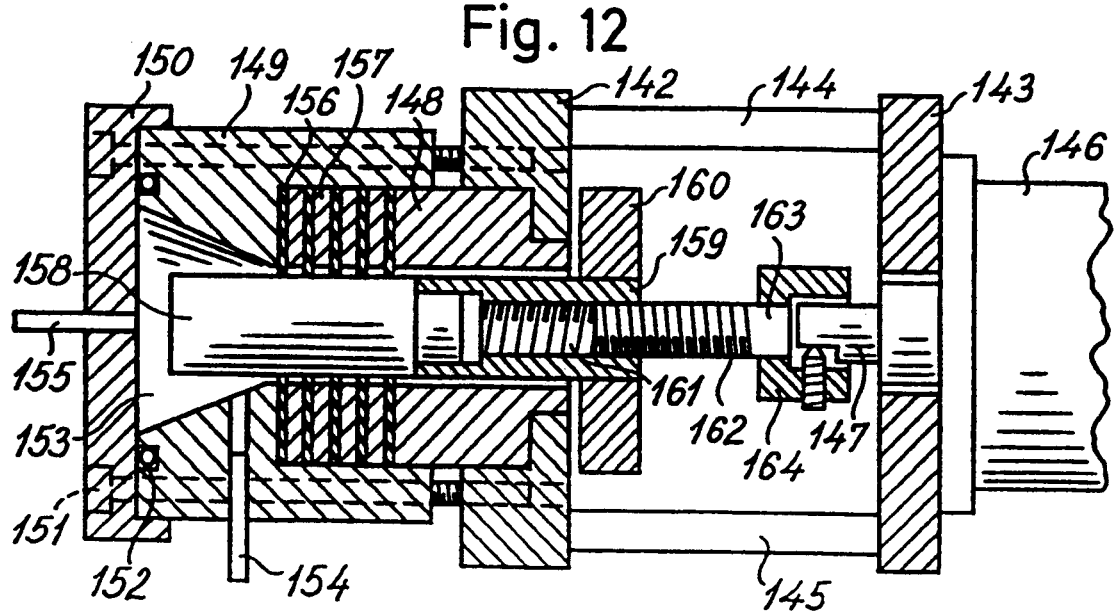
Figure 13:
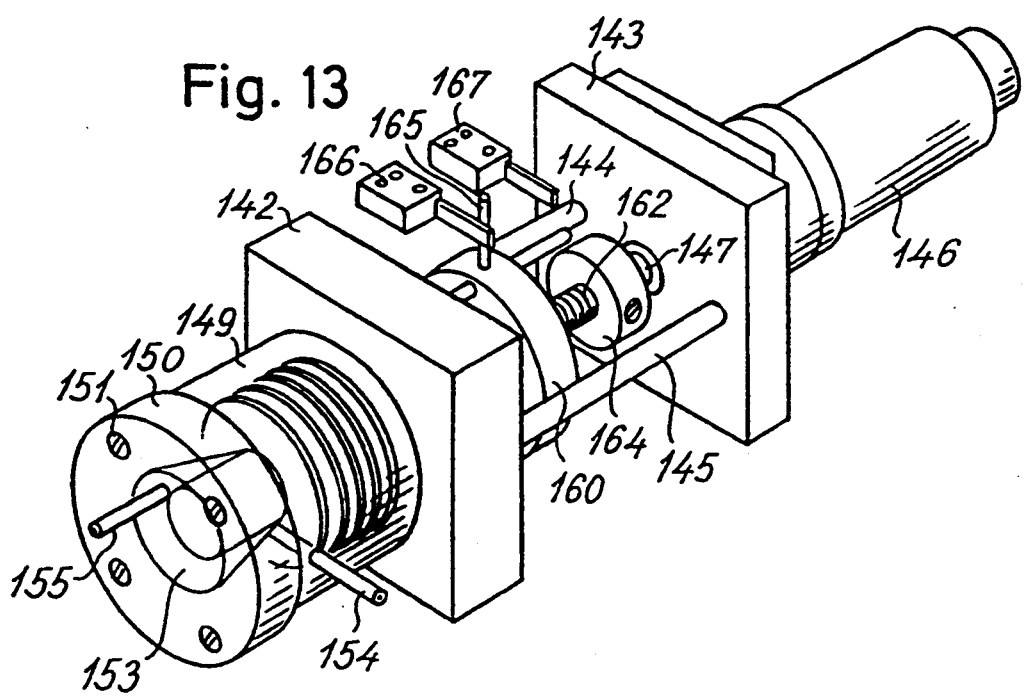
Figure 14:
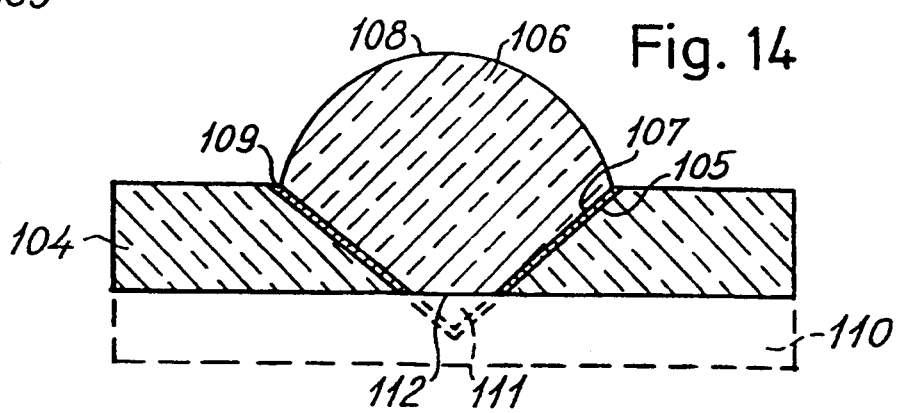
Figure 16:
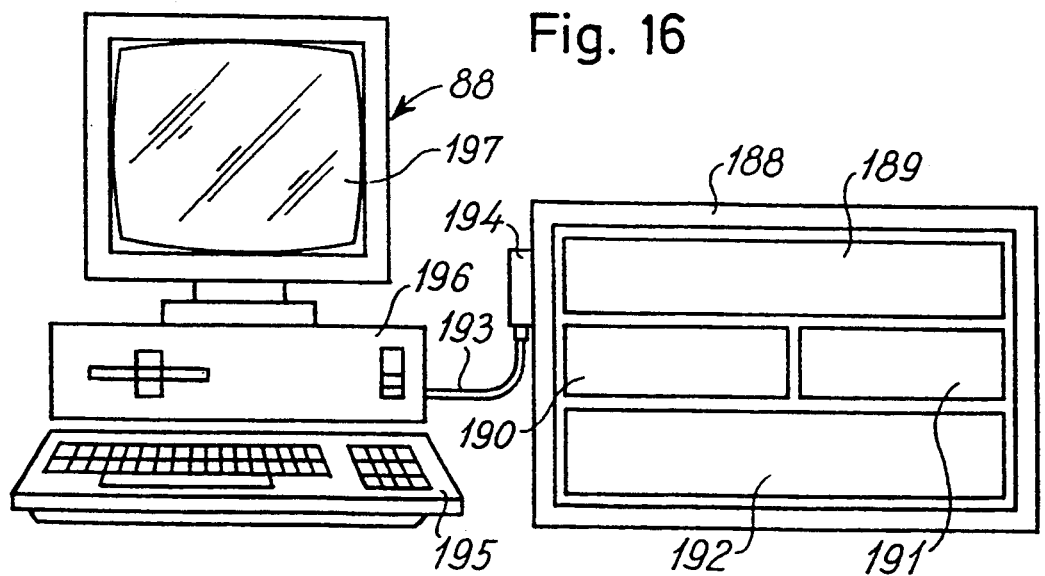
Figure 22:
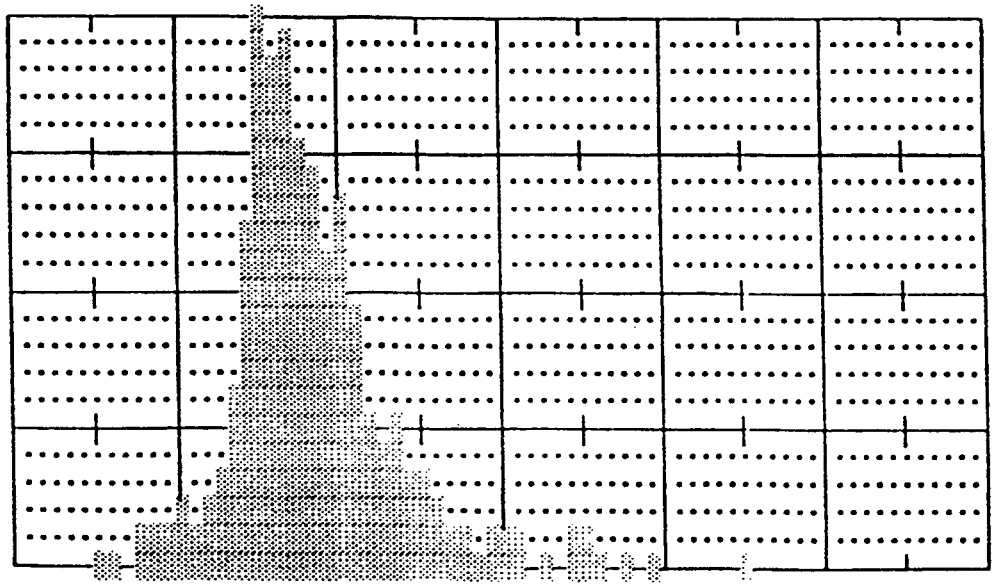

The invention will be further described with reference to the drawings, in which FIG. 1 is a schematical view of a measuring system according to the invention, FIG. 2 is an isometric view illustrating some details of a cuvette of the measuring system shown in FIG. 1, FIG. 3 is a cross-sectional view illustrating parts of the cuvette and of a sample reservoir for supplying a specimen, FIG. 4 is a cross-sectional view of a specimen feeding passage, FIG. 5 is a cross-sectional view of the cuvette shown in FIG. 3, FIG. 6 is an isometrically and partly exploded view of the cuvette and of a cleaning brush and parts of an objective, FIG. 7 is a perspective view of a first embodiment of a hose pump of the measuring system according to the invention, FIG. 8 is a longitudinal, cross-sectional view of a measuring passage of the cuvette illustrating a measuring area, FIG. 9 is a cross-sectional view of the measuring passage perpendicular to the longitudinal axis of the measuring passage and on a level with the optical axis, FIG. 10 is a perspective view illustrating a second embodiment of a hose pump of the measuring system according to the invention, FIG. 11 is a schematical view illustrating a part of the measuring system according to the invention, in which part a piston-type pump is employed, FIG. 12 is a cross-sectional view of the piston-type pump shown in FIG. 11, FIG. 13 is a perspective view of the piston-type pump shown in FIGS. 11 and 12, FIG. 14 is a schematical and sectional view of a cuvette plate and an objective lens assembly illustrating an advantageous production technique, FIG. 15 is a longitudinal, cross-sectional view similar to the view of FIG. 8, in which view the assembly shown in FIG. 14, however, is included, FIG. 16 is a schematical view of a test bench setup including a personal computer and electronic apparatuses of the measuring system according to the invention, FIGS. 17, 18, 19, 20 and 21 are diagrammatic views illustrating the electronic circuitry of the measuring system according to the invention, and FIG. 22 is a diagrammatic view illustrating a print out of a test routine carried out by means of the measuring system according to the invention.

Reference is first made to FIG. 1, which illustrates a schematical view of a measuring system according to the invention. The fluid medium in which particles are suspended is transferred from a sample cup 24, which is illustrated in the central, right-hand part of FIG. 1, to a sample reservoir 14 shown in the central upper part of FIG. 1 and further to a measuring cuvette, which is composed of two parts 3 and 4. The specimen is drawn from the two-part measuring cuvette 3, 4 by means of a drainage pump 80 shown in the lower right-hand part of FIG. 1. In the cuvette, an electrical measurement of the specimen is performed by means of electrical circuitry comprised in a measuring block 86. In the cuvette, the specimen is also subjected to an optical measurement, as a lamp 90, shown in the lower part of FIG. 1, emits light to the cuvette through a mirror 97 and through an objective 65, which light is partly reflected from the cuvette. The light reflected from or emitted from the cuvette is detected by means of photodetectors 94 and 96. The measuring signals generated by the photodetectors 94 and 96 and by the block 86 are supplied to a computer 88, which optionally controls the operation of the system and generates indications of the operation of the measuring system. The individual components together constituting the measuring system is to be described in greater details below.

Reference is now made to FIG. 2, which is a perspective view illustrating the central parts of the cuvette. Thus in FIG. 2, a facial surface 10 of a plate 3 constituting one of the two parts or body halves of the cuvette is disclosed. The plate 3 may be made from quartz glass. In the facial surface 10 of the plate 3 a channel-shaped groove 1 is provided, which may e.g. be formed by a cutting or milling operation, e.g. by means of a cutting tool or the like. In the preferred embodiment of the system according to the invention, the groove 1 constitutes a section of a rectilinear cylinder having a circular cross section of a radius of curvature of approximately 50 $\mu$m, a depth from the facial surface 10 less than approximately 40 $\mu$m, such as 30–35 $\mu$m, and a width at the facial surface 10 of approximately 100 $\mu$m. This configuration has been found suitable for measuring particles having overall diameters of approximately 8–15 $\mu$m or less.

Three continuous or through-going bores 7, 8 and 9 and two cylindrical electrode bodies 5 and 6 are provided extending perpendicular to the facial surface 10 of the plate 3 and aligned with the groove 1. The continuous bore 8 shown in the upper part of FIG. 2 constitutes a feeding passage for the feeding or supply of a diluent, the continous bore 7 constitutes a feeding passage for the feeding or supply of the specimen to be analyzed, and the continous bore 9 shown in the lower part of FIG. 2 constitutes a drainage passage. All three passages may be of cross-sectional dimensions of e.g. approximately 1 mm. The electrodes constitute two cylindrical rods which have been pressfitted or cast into through-going bores. The electrodes 5 and 6 may e.g. be constituted by platinum rods of a diameter of approximately 0.4 mm, and the distance or spacing between the outer surfaces of the rods may e.g. be less than approximately 0.2 mm, such as 0.08 mm. As is evident from FIG. 2, the groove 1 extends through the electrodes 5 and 6. Thus, the groove 1 is preferably cut or milled after the rods 5 and 6 are pressfitted into the through-going bore or after the rods 5 and 6 are solidified, and after the facial surface 10 has been subjected to a face grinding. The continous bores 7 and 8 may suitably be machined before the face grinding of the facial surface 10.

Reference is now made to FIG. 3, which discloses the two-part cuvette 3, 4 in greater details. The plate 3 is received in and fixed to a movable collar 26, which is movable or displaceable relative to a stationary collar 27. An O-ring 28 is arranged circumferentially encircling the movable collar 26. A planar plate 4 of a transparent material such as quartz glass is arranged adjacent to the exposed, facial surface 10 of the plate 3. The plate 4 is preferably face ground and has parallel outer surfaces, one of which is designated the reference numeral 25 and faces the facial surface 10 of the plate 3. The other outer surface of the plate 4 is arranged adjacent to and in contact with an outer plane surface of an objective lens 65. The plate 4 and the objective lens 65 together constitutes an integral assembly. The assembly constituted by the plate 4 and the objective lens 65 is arranged in an lens holder 61, the front part of which is shown in FIG. 3. The lens holder 61 is received in a protecting collar 31 by means of an annular slip gasket 32, which protecting collar 31 is firmly and closely fitted to the stationary collar 27.

In FIG. 3, the lens holder 61 is shown in a position in which it is somewhat retracted from the plate 3, as is the case during a normal cleaning operating procedure, in which the cuvette parts are cleaned. In FIG. 3, fittings 34 are shown, which fittings are arranged in each of the three bores 7, 8 and 9 and received in the plate 3 so as to connect the bores with tubes or tubings for feeding or discharging liquid as it will be explained in greater details below. In FIG. 3 only a single tube or tubing 13 is shown, viz. the tube or tubing constituting a feeding passage for supplying the specimen to the bore 7. The opposite end of the tube or tubing 13 is connected to an outlet socket 20 of the above-mentioned sample reservoir 14. In the lower right-hand part of the sample reservoir 14 an inlet socket 17 is provided. In the central left-hand part and the upper left-hand part of the sample reservoir 14, two inlet sockets 18 and 19, respectively, are provided for supplying a rinsing liquid and pressurized air, respectively, to the sample reservoir 14 and to the measuring system, as will be explained in greater details below.

The sample reservoir 14 further comprises a agitating system in order to ensure that particles suspended in the fluid medium are transferred from the sample reservoir 14 through the passage 13 in a homogenous suspension and furthermore in order to avoid that the particles stick to one another or block the passage 13. The agitating system comprises a motor-driven agitating magnet 15, which is arranged above the uppermost part of the sample reservoir 14, which magnet 15 is rotating around a basically vertical axis and influences an armature head 16 arranged within the sample reservoir 14 below the agitating magnet 15. An agitating wire 11 is connected to the armature head 16 and extends from the armature head 16 through the sample reservoir 14, through the outlet socket 20, through the passage 13 and through the passage 7 of the plate 3. The outer end 12 of the agitating wire projects from the passage 7 and into a passage 2 (shown in FIG. 8) and preferably contacts the surface of the passage 2, which surface is located opposite to the passage 7 and is constituted by part of the facial surface 25 of the plate 4. The upper section of the agitating wire which section extends through the sample reservoir 14 simulataneously agitates the fluid medium in which particles are suspended in the reservoir 14 so as to avoid any sedimentation of particles in the sample reservoir 14.

In FIG. 4, a cross-sectional view of the passage 13 is shown, in which the agitating wire 11 is received, illustrating that the agitating wire has a generally square cross section. Provided the passage 13 has an inner diameter of 1 mm, the agitating wire 13 preferably has an outer lateral dimension of approximately 0.2-0.5 mm, and particularly an outer lateral dimension of approximately 0.3 mm. The wire 13 may be made from nylon, polypropylene, polycarbonate, Teflon or of a similar material, which, on the one hand, does not swell in water, is compatible to the fluid medium or liquid to which it is exposed and is resilient and flexible, and which, on the other hand, is so strong that it does not twist during the agitating movement or relation. According to an alternative embodiment, the wire has a circular cross section (not shown) instead of a polygonal cross section and has a diameter of approximately 0.2-0.5 mm, preferably of approximately 0.3 mm. A wire having a circular cross-section has been found to produce less acustic and electric noise, and is consequently preferable for particularly critical measurements.

As explained above, the lens holder 61 of the two-part cuvette is shown in FIG. 3 in a position in which the cuvette is cleaned, and in which a cleaning brush 51 in a manner to be explained in greater details below is moved downwardly, while rotating, across adjacent facial surfaces of the plates 3 and 4 and also cleans the outer, exposed surfaces of the groove 1 of the electrodes 5 and 6. In FIG. 3, a spring 37, which is supported by a spring bracket, which is further supported and mounted on a metering screw 38, as will be explained in greater details below, excerts a force through a central supporting sphere 36 and a central pin 30 of the movable collar 26, in which the plate 3 is received and causes that the movable collar 26 is positioned in contact with a number of positioning spheres 29 which are received in corresponding bores of the stationary collar 27. The positioning spheres 29 ensure that the movable collar 26 is placed in a precise and well-defined position by means of the spring loading. In the preferred embodiment a total of three spheres 29 are arranged at a mutually angular spacing of 120° at the outer periphery of the movable collar 26 and fastened to the stationary collar 27 as shown in FIGS. 3 and 5.

Having completed the cleaning operation, the lens holder 61 is moved forwardly, i.e. to the right as shown in FIGS. 3 and 5, and to the position shown in FIG. 5. By this movement, the facial surface 25 of the plate 4, which constitutes the left-hand cuvette body member or part, abuts the facial surface 10 of the plate 3, which constitutes the right-hand cuvette body member or part and presses the right-hand cuvette body member or plate 3 and the movable collar 26 somewhat to the right as shown in FIG. 5 against the spring force of the spring 37, by which movement the positioning spheres 29 are unloaded. Thus, when measuring, the cuvette body members or the plates 3 and 4 are kept in abutting arrangement by the force generated by the spring 37, which force is exerted centrally on the right-hand cuvette body member or plate 3, and consequently, the cuvette assembly makes it possible to compensate for small variations or angular inaccuracies and to obtain a perfect, closely fitted facial contact between the facial surfaces 10 and 25 of the two plates 3 and 4, respectively, which together constitute the cuvette. The agitating wire 11 is preferably adapted to project from the passage or bore 7, when the cuvette is being opened, e.g. by 1-3 mm, and to pull back the outer end 12 in the direction towards the passage or bore by contacting the facial surface 25 of the opposite cuvette body member or plate 4, when the cuvette assembly is being closed.

Reference is now made to FIG. 6, which in greater details illustrates mechanical details of the cuvette structure or assembly. At the center of FIG. 6 a stationary, box-shaped cuvette bracket 33 is shown, in which the stationary collar 27 is arranged. In the upper left-hand part of FIG. 6 the plate 3 is shown, which is received in and fixed to the movable collar 26. In FIG. 6, the displaceable or movable parts are shown in their completely retracted positions so as to disclose two of the positioning spheres 29. In the uppermost left-hand part of FIG. 6, the spring bracket 39 is illustrated, which as indicated above constitutes the fixed contact surface of the spring 37, and the metering screw 38 for adjusting the spring tension and consequently the force generated by the spring 37. In its operating position, the spring bracket 39 is fixed relative to the cuvette bracket 33, e.g. by means of screws or any other suitable means.

In the lower part of FIG. 6, a section of the optical system comprising particularly the lens holder 61, which supports the plate 4 and the objective lens 65 (indicated by a dotted line in FIG. 6) is shown. The lense holder 61 is received in and fixed to a bracket 60, which is journalled on guiding tracks 63 and is displaceable or movable in a direction parallel to an optical axis 67 of the optical measuring system relative to the stationary bracket 62 by means of a motor 64, by means of which the plate 4 is displaced or moved in directions towards and from the adjacent plate 3, as explained above with reference to FIGS. 3 and 5.

FIG. 6 further illustrates the cleaning brush 51, which is caused to rotate by means of a brush actuator 52 and which is supported by a brush-actuator supporting bracket 53. The bracket 53 is journalled on guide tracks 54 and is displaceable upwardly and downwardly in a direction substantially parallel with the facial surfaces 10 and 25 of the plates 3 and 4, respectively, by means of a displacement actuator 55. By this arrangement the facial surfaces 10 and 25 of the cuvette body members or plates 3 and 4, respectively, are cleaned in the position in which the cuvette body members or plates 3 and 4 are separated from one another (cf. FIG. 3) by means of the cleaning brush 51 rotatating and simultaneously moving fairly slowly downwardly between the facial surfaces of the plates 3 and 4 and up again. During the cleaning operation a rinsing liquid is injected towards the facial surfaces of the plates 3 and 4, which rinsing liquid is discharged in the cleaning operation as will be discussed below.

Reference is now made to FIG. 7, which shows a hose pump 41 of a type which may be utilized in the measuring system according to the invention. The hose pump 41 comprises, as shown in FIG. 7, a motor 43, which causes a rotor 44 to rotate relative to a rotational axis 45. The rotor 44 is provided with pressure rollers 46, the axes of which extend radially from the rotor. A stationary component of the hose pump 41 is shown below the rotor 44, which component comprises a generally cylindrical body 40 having a radially projecting, disc-shaped abutment collar 48 which supports a tube 42 which extends through holes 47 in the abutment collar 48 and which is tightened around a groove 49 arranged in the peripheral upper surface of the cylindrical body 40. The movement of the tube 42 is limited downwardly in the longitudinal direction of the rotor axis by the abutment collar 48 and upwardly in the longitudinal direction of the rotor axis by a tube-retaining edge 50. The tube 42 is tightly mounted so as to be stretched along the entire circumference by tensile stress. The tube may be retained by tensile stress only by means of the friction of the holes 47, provided that a tube of a suitable dimension and resilience is utilized, and provided that the holes 47 are adapted to this dimension and resilience.

The pressure rollers 46 influences the tube axially so as to flatten the internal aperture of the tube completely at a section below each roller, so as to produce a peristaltic pumping action when the rotor 44 rotates. Due to the tensile stress of the tube, the tube is influenced by the force of friction between the tube-retaining edge 50 and the abutment collar 48 across the entire circumference so that it is completely stable. By these provisions a more continuous and well-defined pumping action and a more continuous pumping process are achieved as compared to the pumping action and the pumping process which is obtainable by means of the hose pumps well-known within the art, in which pumps the tubes normally tend to move relative to the groove when inflated. In the embodiment shown in FIG. 7, the hose pump comprises a total of four pressure rollers, which are arranged at an angular spacing of 90°.

This hose pump ensures a continous and well-controlled pumping, however, a discontinuity cannot be totally avoided whenever a roller rolls accross the section of the discharge holes 47, and consequently the tube bends. When a pressure roller leaves one end of the tube and hits the opposite end, a step-wise variation of the tube pressure is unavoidable. If the flow rate preferably is to be completely steady, this may be achieved by measuring only during the time intervals between the passage of the pressure rollers across the tube bends, i.e. in four periods per turn of the rotor 44 shown in FIG. 7. However, these time intervals are fairly short, but this situation may be improved by means of a special hose pump, which is shown in FIG. 10, This hose pump, which is designated the reference numeral 35 in its entity, differs from the hose pump shown in FIG. 7 in that only two pressure rollers are provided having axes arranged 60°–90° spaced apart. Hereby a suitable time of measuring is achieved with a completely continuous liquid flow during one rotation of the rotor 44 at approximately 240°–270°, viz. 270°–300° minus the period, which is required for the pressure roller to move across the tube bends at the discharge holes 47.

Reference is now made to FIG. 8, which is a schematical and sectional view of the cuvette assembly. In FIG. 8, the plane extends longitudinally through the center of the groove, which defines the capillary passage 2 together with the facial surface 26 of the plate 4 perpendicularly to the facial surfaces 10 and 25 of the plates 3 and 4, respectively. FIG. 8 basically serves the purpose of illustrating the movement of the particles through a measuring zone. The plate 3, which constitutes a first cuvette body half, in which the groove 1 is machined, is shown in the lower part of FIG. 8, and the plate 4, which constitutes a second cuvette body half, is shown in the upper part of FIG. 8. The objective lens 65 is arranged in contact with the plate 4 as discussed above. In FIG. 8, the optical axis 67 is also shown. When performing optical measurements, light is emitted through the objective lens 65 along the optical axis 67, by which emission a section of the passage 2 encircling the optical axis 67 is illuminated. The light which is detected by the photodetectors 94 and 96 is reflected light which is reflected along the optical axis 67.

In the lower left-hand part of FIG. 8, the bore or passage 8 for feeding the diluents, the bore or passage 7 for feeding the specimen, the first electrode body 5, the second electrode body 6, and the bore or passage 9 constituting a drainage passage are shown. In the lower part of FIG. 8, the fittings 34 are received in the respective bores or passages so as to enable that the above-mentioned tubes or tubings may be connected to these fittings 34. A section of the agitating wire 11 is shown in the bore or passage 7, the outer end 12 of which agitating wire extends to and contacts the facial surface 25 of the plate 4 as discussed above. In FIG. 8, it is also indicated, how the wire, being a wire of polygonal cross section, is twisted during the agitation movement. The bores 7, 8 and 9 preferably have diametres of the order of 1 mm, whereas the depth of the groove 1 and consequently of the capillary passage preferably is of the order of 30–35 $\mu$m, by which it is be understood that there exists a risk of blocking the capillary passage. Blocking of the capillary passage may particularly occur at sections where the particles are to pass into the capillary passage 2, and accordingly is is essential that the agitating wire 11 influences the section of the passage 2 at the bore 7, i.e at the section in which the particles of the specimen are introduced into the capillary passage.

If necessary, the diluent may be added through the bore or passage 8 at the upstream end of the capillary passage 2 and may be mixed with the specimen downstream along the capillary passage 2. A plurality of arrows, one of which is designated the reference numeral 68, indicates the flow path through the bores 7 and 8, through the capillalry passage 2 and through the bore 9. The reference numeral 66 indicates particles suspended in the liquid, which is introduced into the capillary passage 2 through the bore 7. The flow of liquid and particles suspended therein are subjected to an electrical field, which is generated between the electrodes 5 and 6, as indicated by lines of flux 69, which extend along the passage 2 with the exception of two end sections adjacent to the electrodes 5 and 6, in which end sections the lines of flux bend towards the surfaces of the electrodes 5 and 6. The electrodes are utilized to measure the conductivity of the liquid by a method well-known in the art, e.g. by supplying a contant voltage or a constant current to the electrodes and by measuring the electrical current. As the liquid is electrically conducting, and as the particles 66, to no substantial extend, may be moved by the electrical field, a measuring result is obtained, which is indicative of and is proportional to the volume of the particles, when within the electrical field.

If the particles pass individually, so that only a single particle is within the electrical field at a specific time, and if the field is well-defined, an electrical signal, which may be converted directly into the volume of the particle, is obtainable.

The measurement implies the generation of exactly the same electical field onto each particle and onto all parts of a particle, and it is therefore to be expected that a not entirely homogeous field will cause an inaccurate measurement, since the particles which pass in the upper section of the capillary passage are exposed to a lower electrical field strength or stay in the electical field for a shorter period of time than the particles which pass in the lower section of the passage. However, it has surprisingly been found that extremely reliable, reproducible and accurate electrically measuring results are achievable by the above-described embodiment of the electrodes, which measuring results are not substantially influenced by edge effects or inhomogenities of the electrical field.

It is believed that this result may be explained by the field extending in a manner so as to be basically homogenous at the section between the electrodes as the lines of flux are directed parallel to the direction of flow of the particles. In the presently preferred embodiment of the measuring system, the shortest distance between the electrodes is 0.08 mm, whereas the depth of the capillary passage 2 is 30–35 $\mu$m as explained above. Therefore, it is obvious that the results of the electrical measuring correspond to the particles passing a homogenous field, which has a length of approximately 0.12–0.35 mm. Another essential point is that the particles, since the flow of liquid exhibit a laminar flow behaviour, tend to be centered towards the centre of the capillary passage, in which the velocity of the flow of liquid is highest. Consequently, the particles tend to follow at exactly the same path.

A determination of the particle volume by measuring the conductivity of the particle is, of course, only possible provided only a single particle is exposed to the electrical field at a time. In real life, the distances between the particles will be statistically varying, and accordingly particle coincidence cannot be completely avoided. The frequence of particle coincidence may, however, be reduced to an acceptable level such as approximately 2% by diluting the specimen, so that the average distance between the particles may be e.g. 2.5 mm. By a flow rate of liquid of the order of 1 m/s the above-indicated average distance corresponds to a particle flow of the order of 400 particle passages per second. If only particles that by measurement of the conductivity of the particles are found to have volumes within a specific interval of volumes are to be subjected to optical measurement, the number of measured particles will in real life be smaller. If e.g. only every tenth particle has a volume within the relevant interval of volumes, an analysis of 5000 particles may be carried out in approximately 2 minutes, and within this period of time 50,000 particles have passed the capillary passage 2. If two particles succeed one another in immediate succession, this may be detected by means of the electical signal exhibiting a step-wise alteration each time a particle enters of leaves the electrical field. Consequently, it is possible electronically to accept measuring signals which correspond to the passage of a single particle through the field, whereas all other measuring signals are suppressed.

When a particle has passed the electrical field, the particle moves further along the capillary passage 2 as indicated by the arrow 68 and passes the optical axis 67 as indicated in FIG. 8. Here it is illuminated by means of rays of light, and the light which is reflected along the the optical axis 67 is detected by the photodetectors 94 and 96 of the measuring system, and electrical signals generated by the photodetectors 94 and 96 are analyzed in order to determine if the particles fluorescence. The colour of fluorescence may also be determined, e.g. by means of an optical system which measures the intensity of light within two or more specific spectral bands. This arrangement serves the purpose of determinating or classifying the particles. From the combined electrical and optical measurements, in combination with information regarding the volume of liquid, the concentration of relevant fluorescent particles suspended in the liquid is derived.

In the embodiment shown in FIG. 8, the exposed outer surface of the electrode 6 acts as a light reflector, and as evident from the cross-sectional view of FIG. 9, the surface design causes a concentrating reflector effect so that the light converges, by which means a high intensity of light is achieved in the measuring area. The facial surface 10 of the plate 3 surrounding the light-reflecting electrode 6 does not fulfil any reflecting function and is preferably adapted to absorbe light. In the embodiment of the two-part cuvette 3, 4 shown in FIGS. 8 and 9, the passage 2 may have a radius of curvature of 50 $\mu$m and a depth of 30–35 $\mu$m, whereas the width of the passage may be of approximately 100 $\mu$m, which is suitable for analyzing particles having diameters of the order of 8–15 $\mu$m or less, as explained above.

By means of the above-described assembly comprising the two-part cuvette 3, 4 and the objective lens 65, in which assembly the objective lens 65 is arranged in intimate contact with the plate 4 of the two-part cuvette 3, 4, in combination with the partial converging-lens effect of the second electrode 6, a very advantageous light utilization is obtained. Accordingly, it is possible to obtain good results when emitting light by means of a iodine quartz photoflood lamp of a rating of 100 W. The measurements may be correlated precisely with the individual particles, since the time, at which the particle passes through the electrical field, is well-known, and since the period of time required for the particle to move from the electrical field to the optical axis is also well-known.

As mentioned above a iodine quartz photoflood lamp may be utilized for exposure or for illuminating. However, a laser lamp, e.g. an argon laser, may also be applied. According to an alternative embodiment, the illuminating system comprises a flash lamp, e.g. of the xenon type, which is ignited after a predetermined delay, when a particle of a suitable size has been detected in accordance with the conductivity measurement. Since the flow rate of the fluid medium in which the particles are suspended is well-known, it is possible to adapt the delay in a manner that the flash light illuminates the particle exactly when it reaches the optical axis 67. By these means a very powerful illumination of the particles is achieved at low costs and by means of a limited consumption of electrical power, and thus low-level, optical signals are detectable. The electrical circuit comprised in the block 86 shown in FIG. 1 and to be described below with reference to FIGS. 16–21 is adapted to activate the flash lamp for emitting as many as 100 synchronized light flashes per second. Furthermore, by employing a periodically ignited or activated flash lamp, heating of the specimen is reduced as compared to a constant illumination of the measuring zone.

Now reverting to the overall schematic view of the presently preferred embodiment of the measuring system according to the invention shown in FIG. 1, a specimen is extracted from the sample cup 24, which contains a fluid medium or a liquid in which particles to be analyzed are suspended. By means of a suction device comprising a lifting device 70 and a submersible suction tube 83, which is submerged into the sample cup 24, the submersible suction tube 83 is connected directly to a suction duct 23, through which the specimen is passed to a particle filter 22, which serves the purpose of retaining particles having volumes bigger than a predetermined volume or diameter, e.g. particles of diameters larger than 20$\mu$, whereupon the specimen is passed through an inlet valve 89 to the inlet socket 17 of the sample reservoir 14.

On the left-hand side of the sample reservoir 14 a light source 56, e.g. a light emitting diode or LED, is arranged, which light source 56 emits light which is passed through the sample reservoir 14, which is made from light-transparent material or which comprises a wall section of a light-transparent material, adjacent to which wall section the light source 56 is arranged, towards a photodetector 57, by means of which photodetector 57 the supply of the fluid medium or the liquid from the cup 24 to the sample reservoir 14 is controlled, as the supply of the liquid from the cup 24 to the sample reservoir 14 is interrupted as the liquid level of the sample reservoir 14 exceeds the liquid level defined by the optical light path from the light source 56 to the light photodetector 57.

The socket 18 of the sample reservoir 14 is connected to a flush pump 74, e.g. a hose pump of the type described above with reference to FIG. 7. The inlet of the flush pump 74 communicates with a valve-controlled vent 72 and with a tank 73 containing a rinsing or cleaning fluid through a heated liquid container 79, from which pre-heated rinsing or cleaning fluid is supplied to the socket 18 of the sample reservoir 14 through a valve-controlled conduct or tube. The flush pump 74 is a reversible pump and is applied when absorbing liquid from the cup 24, during which operation the valve-controlled conduct or tube establishing communication between the heated liquid container 79 and the socket 18 is closed and during which operation the valve-controlled vent 72 is open.

As the optical light path from the light source 56 to the light photodetector 57 is interrupted as the liquid level raises within the sample reservoir 14, the flush pump 74 is stopped, the inlet valve 89 is closed, and the valve-controlled vent 72 is also closed or blocked.

The socket 19 of the sample reservoir 14 is connected to a source of pressurized air or a compressor 71 and to a valve-controlled vent 72'. The transfer of the specimen from the sample reservoir 14 to the two-part cuvette 3,4 is accomplished in the following three-step procedure. Firstly, the air compressor 71 is activated for generating pressurized air, e.g. of approximately 1 bar above the atmospheric pressure. While the air compressor 71 is activated for generating pressurized air, the valve-controlled vent 72' is closed so as to supply the pressurized air generated by the air compressor 71 to the sample reservoir 14. Secondly, the two-part cuvette 3, 4 is open for a short period of time of the order of 20 ms as the lens roller 61 supporting the plate 4 is moved away from the plate 3, as explained above with reference to FIGS. 3 and 4, by which opening the specimen is forced through the feeding passage 13 so as to discharge or vent air trapped within the passage 13 to the atmosphere. Thirdly, after the two-part cuvette 3, 4 is closed after the above-described opening of the cuvette for venting air trapped within the passage 13 and filling the passage 13 with the specimen from the sample reservoir 14, the specimen contained within the sample reservoir is drawn or sucked into the capillary passage 2 shown in FIG. 8 of the two-part cuvette 3, 4 from the sample reservoir 14 and through the feeding passage 13 and further through the bore or passage 7, as a drainage pump 80, which is connected to the bore or passage 9 through a drainage passage 21 is activated. The drainage pump 80, which is implemented as a hose pump of the type described above with reference to FIG. 10, is operated at a well-defined velocity and accordingly controls the flow rate of the liquid through the capillary passage 2 shown in FIG. 8 of the two-part cuvette 3, 4. The drainage pump 80 is further connected to a waste container 81.

The bore or passage 8 of the measuring cuvette 3, 4 communicates with a tank 75 containing a diluent, which may be propelled by means of a pump 76, which is also implemented as a hose pump of the type described above with reference to FIG. 10.

In the measuring phase, the specimen is supplied to the passage 2 of the measuring cuvette 3, 4 from the sample reservoir 14 through the passage 13 interconnecting the outlet socket 20 of the sample reservoir 14 and the bore or passage 7 of the measuring cuvette 3, 4 propelled by the pressurized air, which is supplied to the sample reservoir 14 from the pressurized air source or compressor 71. The flow of liquid through the passage 2 of the cuvette 3, 4 is controlled by the drainage pump 80, which is operated at a constant rotational speed for generating a contant flow rate through the passage 2 of the measuring cuvette 3, 4. During the measuring phase, the pump 76 may be activated for supplying the diluent from the tank 75 to the passage 2 of the measuring cuvette 3, 4 in order to alter the dilution ratio of the specimen which is transferred through the passage 2 of the measuring cuvette 3, 4. The pump 76 may be operated at a variable rotational speed, be accelerated or decelerated or stopped during the measuring phase in order to generate a fairly constant dilution ratio of the specimen which is transferred through the passage 2, or at least in order to provide an adequate dilution ratio for ensuring that the particles of the specimen are transferred through the passage 2 individually and sequentially in order to render it possible to subject the particles individually to the electrical field generated by the electrodes 5 and 6 within the passage 2 and to expose the particles individually to the light flash, still ensuring a constant flow rate through the passage 2, which constant flow rate is of the utmost importance in order to guarantee that the particles that are transferred through the passage 2 are shifted from exposure to the electrical field to exposure to the light flash within a predetermined and fixed period of time.

In case the passage 2 of the measuring cuvette 3, 4 is blocked or in case the feeding passage 13 is blocked, which blocking is detected as no particles are transferred through the passage 2 giving origin to the detection of particles passing through the electrical field generated by the electrodes 5 and 6, the blocking is easily eliminated by carrying out the above-described second step of the feeding procedure, i.e. by opening the two-part cuvette 3, 4 for a short period of time, e.g. of the order of 20 ms, by which opening the blocking is eliminated, as the particles blocking the capillary passage 2 or the feeding passage 3 are expelled from the two-part cuvette 3, 4, which is open, or from the feeding passage 13 into the opened two-part cuvette 3, 4. This procedure of eliminating the blocking of the capillary passage 2 or the feeding passage 3 is believed to constitute an extremely advantageous feature of the measuring system as compared to the prior art measuring systems, which lack this advantageous feature or capability or easily eliminating any blocking of the passages of the measuring system. The liquid expelled from the opened two-part cuvette 3, 4 and from the feeding passage 13 is received in a waste container, which communicates with a spillage passage 77 to be described in greater details below.

When a measuring operation has been carried out, the drainage pump 80 is stopped and the pump 76 and the lifting device 70 for lifting the submersible tube 83 are activated. The lifting device 70 comprises a cam follower 85, which cooperates with a cam 84, serving the purpose of causing the submersible tube 83, when raised from the sample cup 24, to swing to a position in which the submersible tube 84 points to a spillage collector 82, which communicates with a spillage conduit 77. The inlet valve 89 is opened, and the pressurized air supplied to the sample reservoir 14 causes the conduit 23 and the submersible tube 83 to be dry blasted, as a possible residue of the specimen contained in the sample reservoir 14 is flushed from the sample reservoir 14 and expelled from the submersible tube 83 to the spillage collector 82.

Subsequently, the valve of the conduit interconnecting the heating container 79 and the flush pump 74 is opened and the flush pump 74 is activated so as to absorb pre-heated rinsing liquid from the heating container 79, in which the rinsing liquid is heated in order to increase the cleaning effect of the rinsing liquid. The rinsing liquid is transferred to the sample reservoir 14 and expelled through the particle filter 22, the conduit 23 and the submersible tube 83 to the spillage collector 82. Subsequently, the flush pump 74 is stopped, and the compressor 71 is activated briefly so as to dry blast the absorption conduit 23 and the submersible tube 83.

The inlet valve 89 is reclosed, and the measuring cuvette 3, 4 is opened as the lens holder 61 supporting the plate 4 is moved to the left. The flush pump 74 is reactivated transferring rinsing liquid to the sample reservoir 14 and expelling the rinsing liquid through the feeding passage 13 into the opened measuring cuvette 3, 4, from which the rinsing liquid is drained through the spillage passage 77. At the same time, the drainage pump 80 is activated for absorbing liquid from the drainage tank 81 so as to discharge the liquid from the drainage tank through the bore or passage 9 to the opened measuring cuvette 3, 4. The cleaning brush 51 is then activated and moves, when rotating, across the facial surfaces 10 and 25 of the plates 3 and 4, respectively, in a manner that the facial surfaces 10 and 26 and the groove 2 including the exposed surfaces of the electrodes 5 and 6 are washed by means of the liquids furnished and subsequently broomed by means of the brush 51. Spillage fluid is discharged through the spillage passage 77 and is pumped away by means of a spillage pump 78, which is operated continuously during the washing or rinsing operation.

It is to be pointed out that a clean rinsing liquid is added from the drainage tank 81 during the above-described washing or cleaning operation or routine. Thus, the quantity of liquid that is transferred through the measuring cuvette 3, 4 when measuring is very small, and preferably so small that it does not fill up the drainage passage 21, nor is mixed with the clean rinsing liquid, which is filled into the drainage tank 81 in advance. Alternatively, a waste reservoir may be provided in the conduct or tube interconnecting the bore or passage 9 and the drainage pump 80. When performing a cleaning operation, the drainage pump 80 is activated so as to transfer a quantity of liquid from the tank 81, which quantity is larger than the quantity of liquid transferred through the passage 2 of the measuring cuvette 3, 4 when measuring. The total result of the operation of the drainage pump 80 is thus a net liquid conveyance from the drainage tank 81 through the measuring cuvette 3, 4.

Ultimatively, the flush pump 74 and the drainage pump 80 are stopped, and the source of pressurized air or the compressor 71 is briefly activated so as to dry blast the sample reservoir 14 and the feeding passage 13, after which operation the cuvette is reclosed so as to be ready for a subsequent measuring operation.

FIG. 1 further illustrates the optical system, which in addition to the components described above with reference to FIG. 6 comprises a stationary housing component 98, in which the light source 90 and the detectors 94 and 96 are arranged. In FIG. 1, a light source-or a xenon flash lamp 90 emits light that passes through an aperture 91, through a colour filter 99 and is directed to a dichroic mirror 97, which projects the light in a direction along the optical axis 67 longitudinally through the housing component 89 towards the objective lens 65 through a suitable optical system comprising focusing lenses and collimators per-se well-known to a person having ordinary skill in the art. The light which is reflected from the cuvette in a direction along the optical axis 67 passes through the objective lens 65. A predetermined spectral range of the reflected light passes through the dichroic mirror 97 and is further transmitted along the optical axis 67 to a second mirror or a so-called beam splitter 92, which mirror allows a first part of the reflected light to pass straight through the second mirror or beam splitter 92, and which second mirror or beam splitter 92 deflects a second part of the reflected light. The first part of the reflected light, i.e. the light passing straight through the beam splitter 92, is directed to a first colour filter 93 and a first photodetector 94 arranged along the optical axis 67. The second part of the reflected light, i.e. the light deflected by the beam splitter 92 is directed substantially perpendicular to the optical axis 67 to a second colour filter 95 and a second photodetector 96. The dichroic mirror 97, the beam splitter 92 and the colour filters 93 and 95 are so-called interference filters, which are adapted to allow the relevant flourescence colours to be reflected, beamsplitted or transmitted, whereas wavelength range of light different from the relevant wavelengths or wavelength ranges are substantially blocked. The optical system is per-se well-known to a person having ordinary skill in the art and needs therefore not to be described in greater details.

In a first embodiment of the optical system, the colour filter 99 and the xenon flash lamp 90 are adapted to illuminate the measuring cuvette 3, 4 by light within the spectral range of 475–495 nm whereas the colour filters 93 and 95 and the beam splitter 92 are adapted so that the first photodetector may register light of the spectral range of 575–640 nm and the second photodetector light of the spectral range of 520–560 nm.

In another embodiment a iodine quartz photoflood lamp of 100 W is used instead of the xenon flash lamp together with the same arrangement of colour filters.

In a third embodiment an Argon laser is used for illumination, which laser emits light of a wavelength of 480 nm.

The measuring block 86 shown in FIG. 1 is connected to the first and the second electrodes 5 and 6, repectively, and is adapted to supply an electrical signal such as an AC or DC voltage or current signal or a combination thereof to the electrodes, e.g. an AC voltage of 9 V and of a frequency of 50–100 kHz, such as 80–90 kHz. The measuring block 86 also includes circuitry for performing the electrical measurement described above, e.g. for determining impedance variations such as by impedances of the order of 10 kΩ–50 kΩ to measure variations of the impedance as small as $10^{-5}$.

The command block 87 shown in FIG. 1 receives the electrical signals generated by the various electrical units of the measuring system, among others the optical system, the measuring block 86, the photodetectors 94 and 96 etc., and generates control signals for controlling the operation of the various components of the measuring system such as the valves, the pumps, the actuators etc., which components all are adapted to be remotely controlled. The command block 87 further constitutes an interface block to the computer 88.

Reference is now made to FIG. 11, which is a schematical view of an alternative embodiment of the fluid-transfer system of the measuring system disclosed in FIG. 1, in which an alternative embodiment of the liquid-transfer system and an alternative and presently preferred embodiment of a pump for transferring fluid or liquid are employed, which pump is a piston-type pump. In FIG. 11, a first piston pump 176 and a second piston pump 180 are employed substituting the hose pumps 76 and 80, respectively, shown in FIG. 1. The containers 75 and 81 shown in FIG. 1 are in FIG. 11 substituted by pressurizable containers 175 and 181, respectively. For pressurizing the containers 175 and 181, the pressurized air conduit interconnecting the source of pressurized air or the compressor 71 and the inlet 19 of the storage container 14 shown in FIG. 1 is provided with a T-shaped connector for supplying pressurized air to the pressurizable containers 175 and 181. The pressurized air conduit supplying pressurized air from the compressor 71 to the containers 175 and 181 is provided with controllable valves for controlling the supply of pressurized air to the containers 175 and 181. Thus, the pressurized air conduit connected to the container 175 is provided with a controllable valve 177, and the pressurized air conduit supplying pressurized air to the container 181 is provided with a controllable valve 178, The conduit interconnecting the piston-type pumps 176 and 180 and the containers 175 and 181, respectively, are also provided with controllable valves designated the reference numerals 179 and 182, respectively. The provision of the pressurizable containers 175 and 181 basically serves the purpose of rendering it possible to vent the piston pumps 176 and 180, respectively, by forcing the liquids contained withing the containers 175 and 181, respectively, into the piston pumps 176 and 180, respectively.

The piston-type pumps 176 and 180 are, however, extremely advantageous as compared to the hose pumps discussed above with reference to FIGS. 1, 7 and 10 in that the piston-type pumps 176 and 180 render it possible to provide an accurate and easily controllable dosage of liquid and consequently an extremely accurate and easily controllable liquid transfer.

In FIG. 12 and 13, the piston-type pump, which is preferably employed in the measuring system according to the present invention as discussed above with reference to FIG. 11, is shown in an elevational, sectional view and in a perspective view, respectively. The piston-type pump is designated the reference numeral 141 in its entity. The piston-type pump 141 comprises two stationary blocks 142 and 143, which are kept in parallel and spaced apart relationship by means of distance rods 144 and 145. A drive motor 146 is fixed to the stationary block 143 by means of screws, threads or alternative, appropriate fixation means and has an output shaft 147, which extends from the drive motor 146 through a through-going bore of the stationary block 143 into the space defined between the stationary blocks 142 and 143. Opposite to the drive motor 146, a piston housing is fixed to the block 142. The piston housing is composed of basically three components, an inner housing component 148, an outer housing component 149 and an end plate 150. The end plate 150 is fixed to the stationary block 142 by means of a total of four screws 151, which extend through through-going bores of the outer housing component 149 for assembling or bolting the end plate 150 and the outer housing component 149 to the stationary block 142. The inner housing component 148 is received within the outer housing component 149 and extends through a through-going, stepped bore of the stationary block 142.

A sealing O-ring 152 is received within a circumferential recess of the outer housing component 149 and serves the purpose of providing a fluid-tight connection between the outer housing component 149 and the end plate 150. Within the outer housing component 149, a frustoconical space is defined, which frustoconical space 153 communicates with two tubes 154 and 155, which extend through through-going bores of the outer housing component 149 and through the end plate 150, respectively. The tubes 154 and 155 are in mutual fluid communication through the frustoconical space 153.

A total of five annular sealing gaskets 156 are in a kept and spaced apart relationship by means of four annular spacers 157 and are received and kept together as a sealing gasket assembly between the inner housing component 148 in the outer housing component 149. Through the annular sealing gaskets 156 and further through the inner housing component 148 and the stationary block 142, a cylindrical passage extends, in which a piston body 158 is movable to and from the end plate 150 for filling out a smaller or larger fraction of the frustoconical space 153. The annular sealing gaskets 156 provide a fluid-tight guidance of the piston body 158 and prevent any leakage of fluid or liquid from the frustoconical space 153.

From the end of the piston body 158 opposite to the end of the piston body 158 facing the inner surface of the end plate 150, a bushing or socket 159 extends into the inner space defined between the stationary blocks 142 and 143 and is fixed to a collar 160. The bushing or socket 159 is provided with an internal thread 161, which measures with an outer thread 162 of a threaded shaft 163, which is fixed to the output shaft 147 of the drive motor 146 by means of a clutch 164.

A highly accurate and easily controllable dosage of fluid may be transferred to or from the piston-type pump 141 through one of the tubes 154 and 155 by moving the piston body 158 away from the adjacent inner surface of the end plate 150 or towards said inner surface by rotating the output shaft 147 of the drive motor 146 in a first rotational direction or in the opposite rotational direction for causing the bushing or socket 159, which is provided with the internal thread 161 meshing with the outer thread 152 of the threaded shaft 153 to move relative to the rotating threaded shaft 153.

As is evident from FIG. 13, the collar 160 may be provided with an outwardly or upwardly protruding rod 165, which serves the purpose of activating a first or a second microswitch 166 and 167, respectively, which serve the purpose of detecting preset end positions of the collar 160 and consequently preset end positions of the piston body 158 within the frustoconical space 153 and consequently deactivate the drive motor 145 in case the piston body 158 is about to be moved into intimate contact with the inner surface of the end plate 150, which might mechanically harm the piston-type pump, or is about to be retracted to far from the inner sealing gaskets 176, which might cause leakage of fluid or liquid from the piston-type pump.

In FIG. 14, a presently preferred method is shown of producing a lens assembly comprising an objective lens and a plate component together constituting a lens assembly serving the same purpose as the lens assembly described above with reference to FIGS. 1, 3, 5, 6 and 8 and comprising the objective lens 65 and the plate 4. Whereas the above-described assembly is composed of identical components, which are glued together by means of a light-transparent glue, the production technique illustrated in FIG. 14 involves assembling the objective lens and the plate by means of non-light-transparent glue for, to any substantial extent, eliminating any light-scattering and light-diverging effects originating from the optical interface between the objective lens and the plate to which the objective lens is fixed. The plate shown in FIG. 14 is substituting the plate 4 described above and designated the reference numeral 104, and is provided with a conical recess designated the reference numeral 105. An objective lens 106 of the assembly shown in FIG. 14 differs from the objective lens 65 discussed above in that the objective lens is provided with an outer conical surface 107 opposite to an outer spherical, convex surface of the objective lens 106. The plate 104 and the objective lens 106 are preferably made from the same material, such as quartz glass, or are made from materials of substantially identical, optical properties. The objective lens 106 is glued to the plate 104 by means of a glue, which provides a light-intransparent layer 109, which bonds the outer conical surface 107 of the objective lens 106 to the conical recess 105 of the plate 104. The glue layer is solidified, a substantial fragment or section 110 of the plate 104 is removed in a grinding process, and a part of the objective lens 106 at the apex 111 of the pyramid defined by the conical surface 107 of the objective lens 106 is also removed. Consequently, a window or an aperture 112 is provided, which constitutes the window or aperture through which light is transmitted from the objective lens 106 to the adjacent passage 2, which is shown in FIG. 15, and furthermore, through which the light is transmitted from the passage, i.e. reflected light, through the objective lens 106.

In FIG. 15, the lens assembly comprising the objective lens 106 and the plate 104 produced as discussed above with reference to FIG. 14 is shown arranged adjacent to the cooperating plate 3 of the two-part cuvette. The cuvette assembly shown in FIG. 15 further differs from the above-described two-part cuvette shown in FIG. 8 in that a total of three electrodes is provided, designated the reference numerals 115, 116 and 117. The electrode 117 primarily serves the purpose of defining a light-reflecting surface identical to the light-reflecting surface defined by the electrode 6 as discussed above with reference to FIGS. 8 and 9. The provision of three or even more electrodes serves the purpose of rendering it possible to refine or elaborate the detection of the transfer of particles through the passage 2 from the inlet bore 7 to the outlet bore 9 by accurately detecting the presence of the particles within the passage 2 by means of two or more electrical fields so as to render it possible to accurately control that the light source is ignited for exposing a particle present within the passage 2 exactly at the time the particle is positioned adjacent to the mirror defined by the electrode 117 and adjacent to the window or aperture 112. Thus, the detection of the presence of a particle within the passage 2 may be established by the generation of an electrical field between the electrodes 115 and 116, and an additional electrical field may be generated between the electrodes 116 and 117 for controlling or surveying the transfer of the particle or particles through the passage 2 past the window or aperture 112 and past the exposed, mirror-defining end surface of the electrode 117.

In FIG. 16, an overall schematical view of a test bench setup of the electronic circuitry of the measuring system described above is shown, which test bench setup comprises the above-mentioned computer 88 and a cabinet 88, in which four electronic apparatuses 189, 190, 191 and 192 are housed. The cabinet 188 and the electronic apparatuses 189-192 housed therein is connected to the computer 88 through a bus cable 193, which is provided with a plug 194, which is received in a mating and cooperating socket of the cabinet 189. The computer 88 basically comprises three sections, viz. a keyboard 195, a CPU (central processing unit) section 196 and a display or CRT (cathode ray tube) 197. The computer 88 is basically of the personal computer or PC-type.

The electronic apparatus 189 constitutes an interface between the electronic, analogue and digital circuitries of the measuring system and the PC or computer 88. In a test bench setup, an interface to IBM PC/XT/AT PCs were established by means of a high-performance, high-speed, multi-function data acquisition card for IBM PC/XT/AT and compatible computers of the type PC-LabCard TM PC 812, which card was mounted within the CPU 196, and by means of a screw-terminal board of the type PC-LabCard TM PCL-780, which card was mounted within the housing 189. The electronic apparatuses housed within the housings 190, 191 and 192 constituted an AD converter (analogue-digital converter), a 24V/4A power supply and a level detector, respectively. The AD converter and the level detector 190 and 192, respectively, are to be described in greater details below. The 24V/4A power supply was a commercially available power supply unit.

Figure 17:
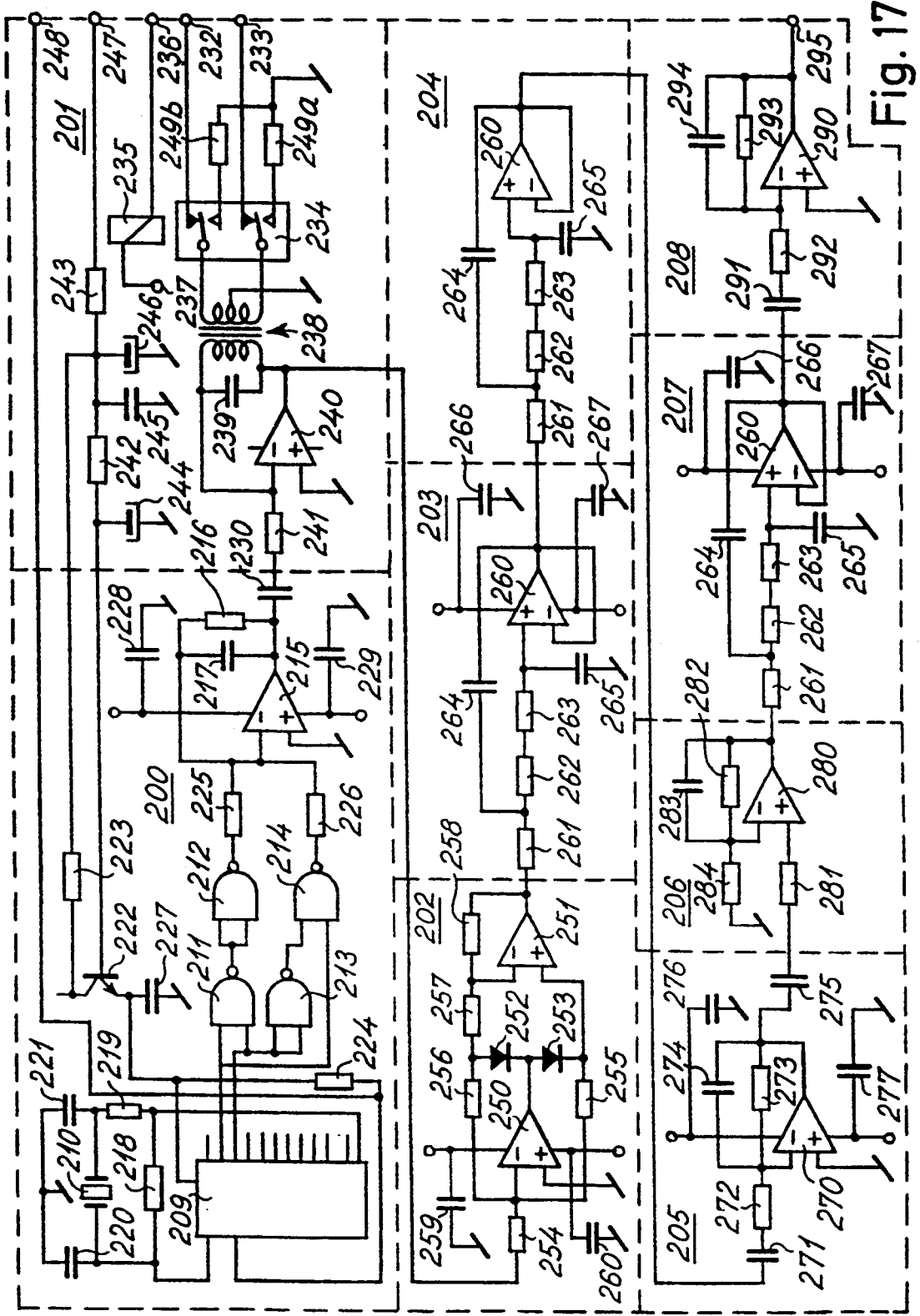

In FIG. 17, a diagrammatic view of a presently preferred embodiment of an electronic circuitry of an electronic apparatus is shown, which electronic apparatus is connected to and communicates with the electrode bodies 5 and 6 shown in FIGS. 3, 4 and 8. The diagrammatic view of FIG. 17 basically discloses nine sub-circuit sections housed within dotted-line boundary lines and designated the reference numerals 200-208, respectively.

The sub-circuit section 200 constitutes an oscillator section including an electronic-oscillator circuit block 209, which is controlled by a crystal 210. The oscillator circuit block 209 generates an output oscillator signal, which is divided into an oscillator signal of a lower oscillator frequency by means of a total of four NAND gates 211-214. The output of the frequency-dividing circuit constituted by the NAND gates 211-214 is connected to an inverting input of an operational amplifier 215, the non-inverting input of which is grounded. The output of the operational amplifier 215 is connected to the inverting input thereof through a feedback resistor 216, which is shunted by a capacitor 217.

The oscillator section 200 further includes two resistors 218 and 219 and two capacitors 220 and 221, which resistors 218 and 219 and which capacitors 220 and 221 are connected in a conventional configuration around the crystal 210. The oscillator 200 additionally includes the following peripheral components: An NPN transistor 222, resistors 223, 224, 225 and 226, and capacitors 227, 228, 229 and 230.

The sub-circuit section 201 basically constitutes a current driver for supplying a constant-current oscillating signal to the electrodes 5 and 6 discussed above. The electrodes 5 and 6 are connected to the subcircuit section 201 through terminals 232 and 233, which are connected to output terminals of a two-position, two-pole relay 234. The relay 234 is energized by means of a coil 235, which is connected to terminals 236 and 237. Provided the relay 234 is activated by energizing the coil 235, the terminals 232 and 232 and consequently the electrodes, such as the electrodes 5 and 6, alternatively the electrodes 116 and 117 shown in FIG. 15, are connected to an output winding of a balancing transformer 238, which output winding provides a symmetrical and balanced drive to the electrode. The input winding of the balancing transformer 238 is shunted by a capacitor 239 and is connected across the output and the inverting input of an operational amplifier 240, the non-inverting input of which is grounded.

The inverting input of the operational amplifier 240 is connected to the output of the oscillator section 200, i.e. the output of the operational amplifier 215, through a series configuration of a resistor 241 and the above-mentioned capacitor 230. Consequently, the impedance across the electrodes, such as the electrodes 5 and 6, alternatively the electrodes 116 and 117 shown in FIG. 15, is connected in a balanced and symmetrical configuration, for providing a common-mode rejection of electrical noise from external sources, across the output and the inverting input of the operational amplifier 240, and consequently constitutes a feedback impedance or resistor.

As will be appreciated, the inverting input of the operational amplifier 240 constitutes a virtual ground to which a current signal is supplied through the resistor 241, which converts the voltage signal supplied by the oscillator 200 into a current signal. Consequently, the operational amplifier 240 presents at its output a voltage signal, by means of which the operational amplifier drives a compensation current to its inverting input through the impedance connected across the output and the inverting input thereof for compensating the current signal supplied to the inverting input of the operational amplifier 240 through the resistor 241.

The output signal generated by the operational amplifier 240 represents the impedance across the electrodes connected to the terminals 232 and 233. The section 201 further includes two resistors 242 and 243 and three capacitors 244, 245 and 246, which resistors 242 and 243 and which capacitors 244, 245 and 246 constitute low-pass filtering components connected to the NPN transistor 222 of the oscillator 200 for low-pass filtering an enable signal, which is supplied to the circuit 201, through a terminal 247. An additional terminal 248 is provided so as to render it possible to reset the oscillator circuit block 209 of the oscillator 200. The section 201 additionally includes two resistors 249a and 249b, which are connected across the output winding of the balancing transformer 238, provided the relay 234 is not activated.

The section 202 basically constitutes a rectifier circuit block comprising two operational amplifiers 250 and 251, two rectifying diodes 252 and 253, a total of five resistors 254, 255, 256, 257 and 258, and further two capacitors 259 and 260. The rectifier 202 is of a conventional circuit configuration and is not to be described in greater details.

The section 203 constitutes a low-pass filter implemented by means of an operational amplifier 260 constituting a second order, low-pass Bessel filter. The low-pass filter 203 further includes three resistors 261, 262 and 263 and four capacitors 264, 265, 266 and 267. The second order, low-pass Bessel filter of the section 203 is of a conventional circuit configuration and is not to be described in greater details.

The sections 204 and 207 also constitute low-pass filter sections, which are identical to the low-pass filter of the section 203. Consequently, the sections 204 and 207 are not to be described in greater details.

The section 205 constitutes a low-noise, 20 dB Gain, inverting amplifier stage comprising an operational amplifier 270 and further an input capacitor 271, an input resistor 272, a feedback resistor 273, a feedback-resistor shunting capacitor 274, an output capacitor 275 and voltage-supply bypass capacitors 276 and 277.

The section 206 constitutes a 20 dB Gain, non-inverting amplifier stage comprising an operational amplifier 280, an input resistor 281, a feedback resistor 282, a feedback-resistor shunting capacitor 283 and a grounding resistor 284.

The section 208 constitutes a 20 dB Gain, inverting-amplifier stage comprising an operational amplifier 290, an input capacitor 291, an input resistor 292, a feedback resistor 293 and a feedback-resistor shunting capacitor 294.

The output of the operational amplifier 290 is connected to an output terminal 295, at which a signal is generated representing the detection of the presence of a particle altering the electrical conductivity of the section of the capillary passage 2, shown in FIG. 8, adjacent to the electrodes 5 and 6, which section is exposed to the electrical field represented by the lines of flux 69, also shown in FIG. 8.

Reference is further made to example 1, in which the components of the sections 200–208 are listed.

It is to be pointed out that the low-pass filter sections 203, 204 and 207 of the electronic circuit shown in FIG. 7 provide an electronic delay of the measuring signal generated by the electrodes connected to the terminals 232 and 233, which delay is of the order of approximately 150 $\mu s$ and has to be taken into consideration in the overall measuring system setup as the delay constitutes a delay of the generation of a detection output signal at the output 295 of the operational amplifier 290 of the section 208 relative to the presence of the particle given origin to the generation of the detection signal at the electrode 5 shown in FIG. 8, during which delay the particle is transferred or shifted through the passage 2 towards the electrode 6, also shown in FIG. 8.

Figure 18:
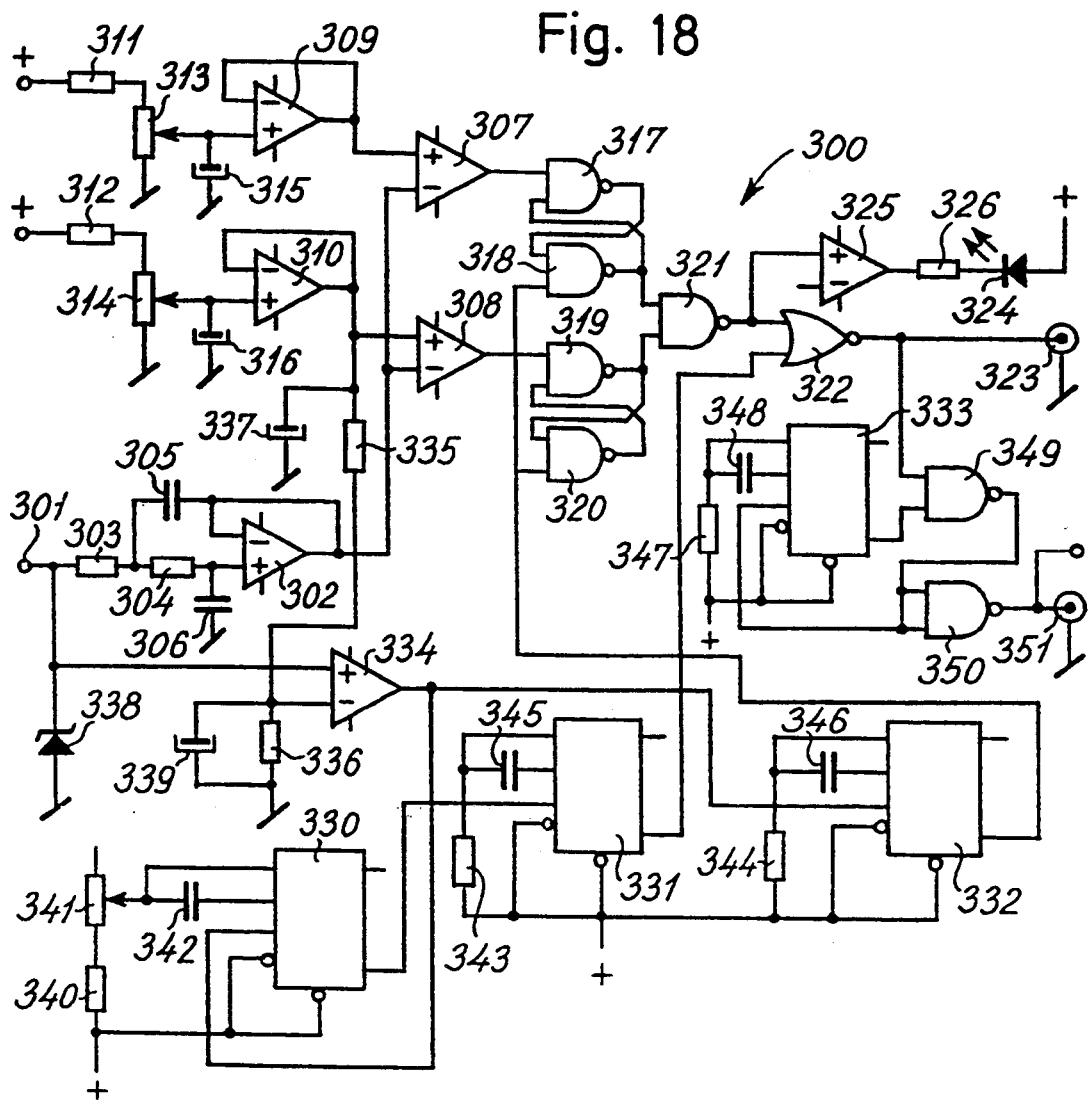

In FIG. 18, an electronic circuit is shown, which constitutes a level detection circuit, to which the output signal present at the output terminal 295 of the electronic circuit shown in FIG. 17 is input. The electronic circuit shown in FIG. 18 is designated the reference numeral 300 in its entity and receives the above-mentioned output signal at an input terminal 301. The input signal presented to the electronic circuit 300 at the input terminal 301 is presented to a second-order, low-pass filter comprising an operational amplifier 302, two input resistors 303 and 304 and two capacitors 305 and 306. The output of the second order, low-pass filter comprising the operational amplifier 302 is input to the inverting input of two comparators 307 and 308, which receive reference voltages at their respective non-inverting inputs from voltage followers comprising unity-gain operational amplifiers 309 and 310, respectively, which reference voltages represent the upper and lower limits, respectively, of the input signal input to the input terminal 301 and further corresponding to a maximum and minimum, respectively, dimension or size of the particles which are to be evaluated and exposed to a flash as discussed above.

The reference voltages supplied to the comparators 307 and 308, respectively, from the voltage followers 309 and 310, respectively, are generated by resistance voltage-dividing networks, each comprising a fixed resistor 311 and 312, respectively, and a variable resistor 313 and 314, respectively, which variable resistors 313 and 314 are shunted by capacitors 315 and 316, respectively.

Provided the signal input to the input terminal 301 is within the voltage range defined by the variable resistors 313 and 314, the low-level comparator, i.e. the comparator 308, detects an input signal supplied thereto from the output of the operational amplifier 302, which input signal exceeds the reference voltage supplied to the comparator 308 from the output of the voltage follower 310, whereas the high-level comparator 307 receives an input signal at its inverting input from the output of the operational amplifier 302, which input signal is lower than the reference voltage supplied to the non-inverting input of the comparator 307 from the output of the voltage follower 309. The output of the comparators 307 and 308 are consequently low and high, respectively. The output of the comparators 307 and 308 are input to a set of logical gates comprising a total of five NAND gates 317-321, and a single NOR gate 322, which logical gates provide a conversion of the logical levels generated by the comparators 307 and 308 into a control signal representing the detection of the presence of particles of a size within the relevant range, which control signal is output for further signal processing at an output 323 and further visualized by an LED 324, which is interconnected between a positive supply rail and the output of the NAND gate 321 through an LED driver comprising an operational amplifier 325 and a resistor 326.

The lower part of the electronic circuit shown in FIG. 18 constitutes a timer circuit, which serves the purpose of, on the one hand, delaying the activation of the flash until the particle that has been detected has moved from its detection position adjacent to the electrode 5 shown in FIG. 8 to a position adjacent to the electrode 6 shown in FIG. 8 and, on the other hand, the purpose of establishing a duty cycle of the flash, which duty cycle constitutes a minimum time period which has to lapse from a previous activation of the flash until the flash is ready to be reactivated. The electronic circuit shown in FIG. 18 consequently comprises four timer blocks 330-333, which timer blocks 330, 331 and 332 serve the purpose of establishing the delay, whereas the electronic timer circuit 333 defines the duty cycle of the flash.

The electronic timer circuits 330, 331 and 332 are further provided with additional peripheral components, viz. a comparator 334, which at its non-inverting input receives the input signal from the terminal 301 and receives the reference voltage generated by the voltage follower 310 through a voltage-divider network comprising two resistors 335 and 336. The output of the voltage follower 310 is further connected to ground through a capacitor 337. The non-inverting input of the comparator 334 and consequently the input terminal 301 is connected to the cathode of a Zener diode 338, the anode of which is grounded. The inverting input of the comparator 334 is grounded through a capacitor 339.

The electronic-timer circuit block 330 is provided with peripheral components, viz. a resistor 340, a variable resistor 341 and a capacitor 342, whereas the electronic-timer circuit blocks 331 and 332 each are provided with a peripheral, passive RC network comprising a resistor 343 and 344, respectively, and a capacitor 345 and 346, respectively. The duty cycle defining electronic-timer circuit block 333 is also provided with a passive RC network comprising a resistor 347 and a capacitor 348 and is connected to two NAND gates 349 and 350. The NAND gate 349 also receives the output signal from the NOR gate 322, i.e. the output signal present at the output terminal 323, whereas the output of the NAND gate 350 is connected to an output terminal 351, which constitutes the output terminal from which the control signal which is supplied to the flash is presented.

Reference is hereby made to example 2 below, in which the components shown in FIG. 18 are listed.

Figure 19:
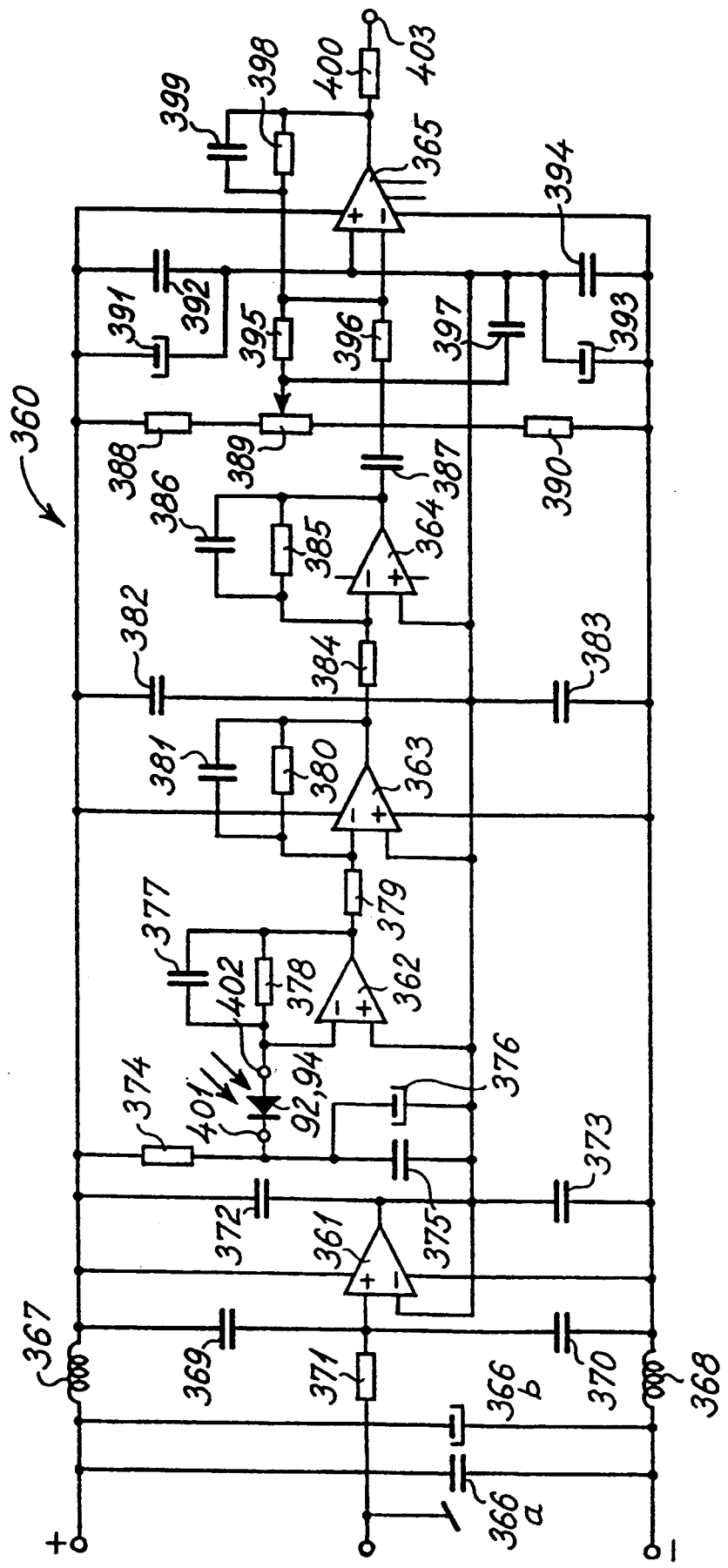
Figure 20:
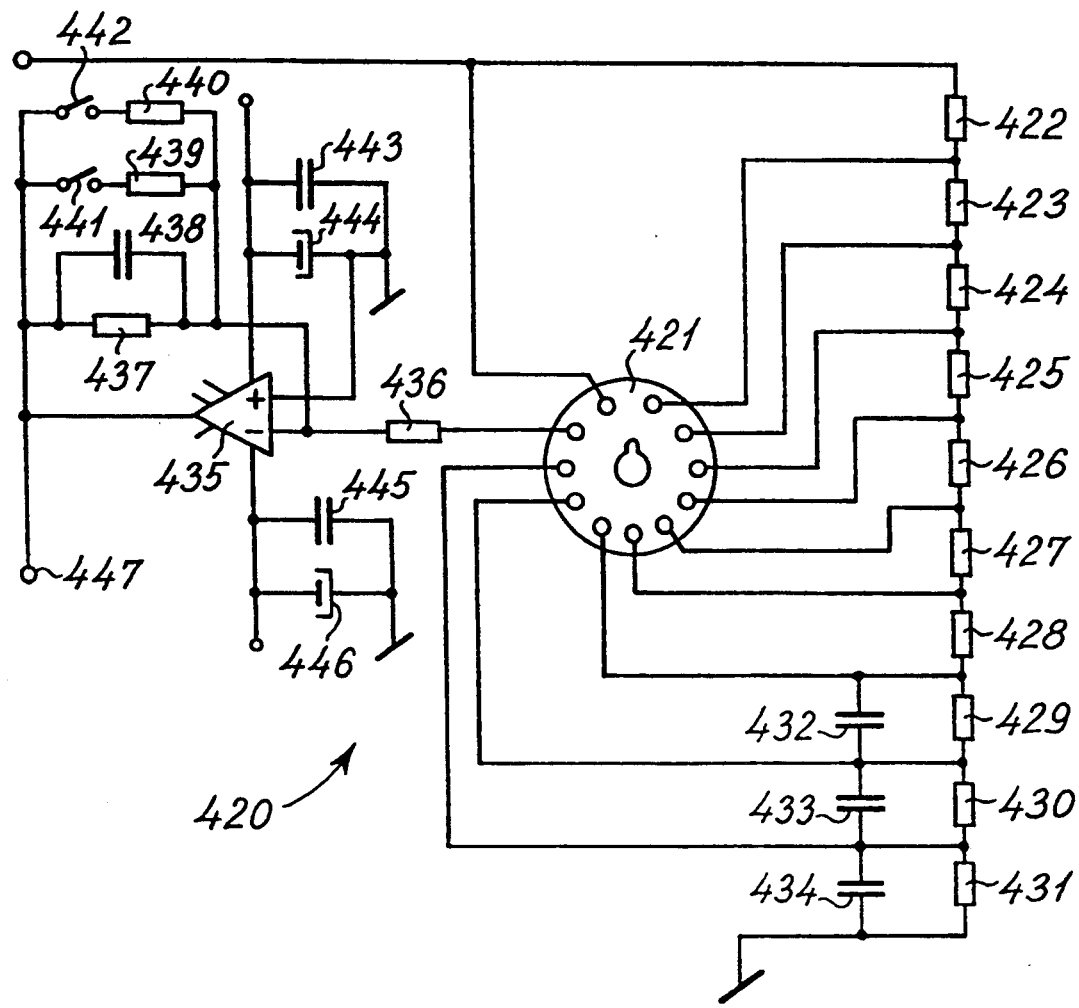

FIGS. 19 and 20 illustrate two circuit diagrammes constituting alternative implementations of photodetectors comprising a photo diode and a multiplier tube, respectively. In FIG. 19, an electronic circuit diagramme designated the reference numeral 360 in its entity is shown, which electronic circuit comprises a photo diode, such as one of the photo diodes 92 or 94, described above. The electronic circuit 360 further comprises a total of five operational amplifiers 361-65, of which the operational amplifier 361 constitutes a ground driver, which constitutes a voltage follower generating at its output a ground voltage level, which constitutes an internal ground level of the electronic circuit 360.

The operational amplifiers 362-365 constitute a four-stage cascade amplifier, each of which stages is implemented as an inverting amplifier. The circuit is of a conventional structure, and reference is made to example 3 below, in which the electronic components identified in FIG. 19 are listed. The electronic circuit 360 shown in FIG. 19 generates at its output 403 a signal in response to the current generated by the photo diode 92, 94, which is connected to the electronic circuit 360 through terminals 401 and 402, which current is converted into a voltage signal and amplified by the four-stage amplifier comprising the above-mentioned, operational amplifier 362-365.

In FIG. 20, an electronic-circuit diagramme designated the reference numeral 420 in its entity is shown, which electronic-circuit diagramme illustrates an implementation of a photodetector including a photo-multiplier tube, which photodetector has been used in the above-described test bench setup. The electronic circuit 420 shown in FIG. 20 centrally comprises the photomultiplier tube 421, which is connected to a resistance divider network comprising ten resistors 422–431 and three capacitors 432–434. The output of the photo-multiplier tube 421 is connected to an inverting input of an operational amplifier 435 through a resistor 436, which operational amplifier 435 constitutes an inverting amplifier stage. The output of the operational amplifier 435 is connected to the inverting input of the operational amplifier through a feedback resistor 437, which is shunted by a capacitor 438. The gain of the inverting amplifier stage constituted by the operational amplifier 435 may be reduced by connecting one or more resistors 439 and 440 across the output of the operational amplifier 435 and the inverting input of the operational amplifier 435 by means of switches 441 and 442, respectively. The non-inverting input of the operational amplifier 435 is grounded, and the power supply rails connected to the operational amplifier 435 are by-passed by capacitors 443–446. The operational amplifier 435 generates at its output, which is connected to a terminal 447, a voltage signal in response to a signal being input to the inverting input of the operational amplifier 435 from the output of the photo-multiplier tube 421 and consequently in response to the detection of light transmitted from the cuvette in response to the ignition of the flash after detection of the particle as discussed above.

Reference is made to example 4 below, in which the components of the electronic circuit diagramme 420 are listed.

Figure 21:
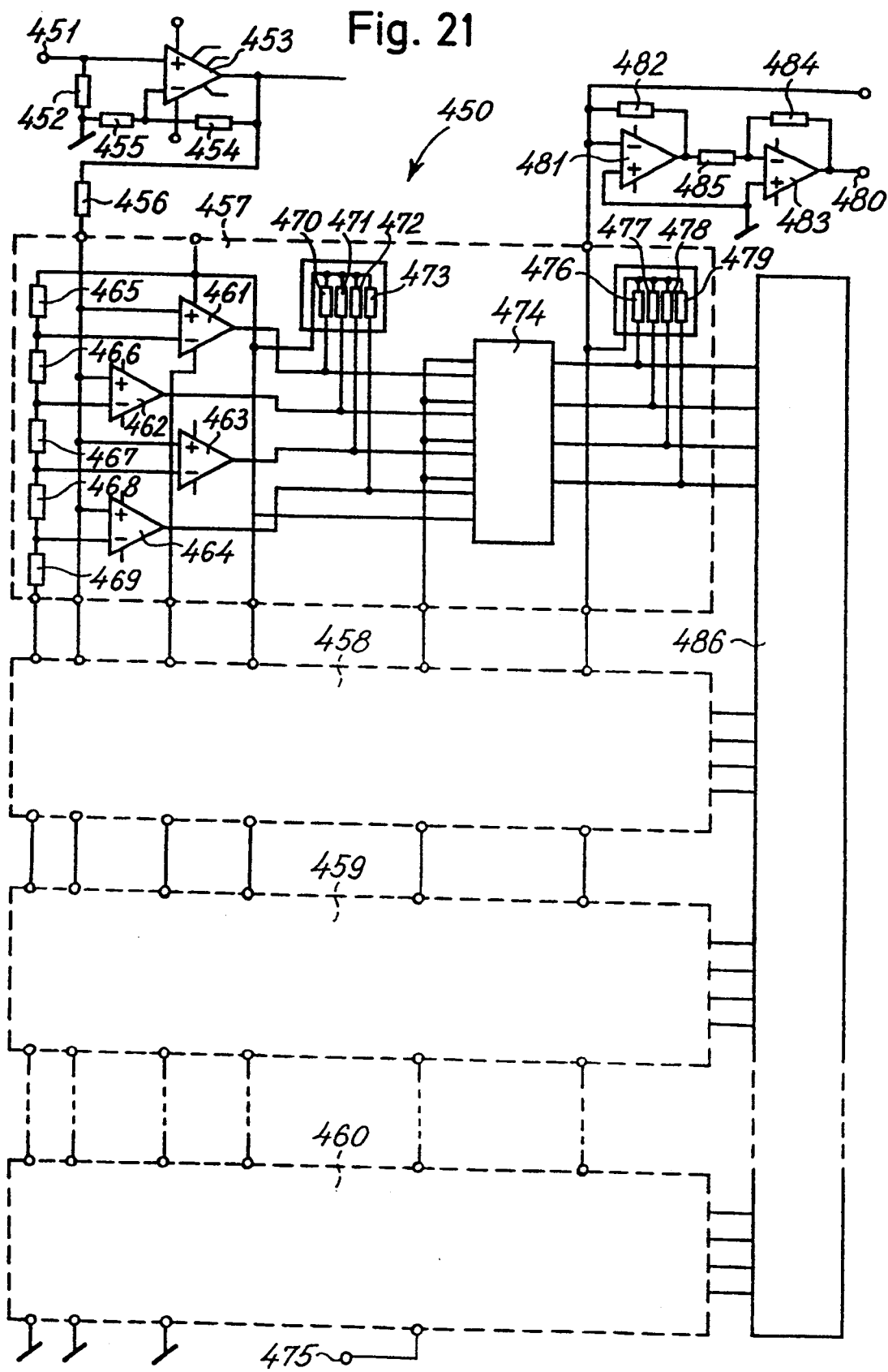

The output signal present at the output terminal 403 of the electronic circuit 360 shown in FIG. 19, or alternatively at the output terminal 447 of the electronic circuit shown in FIG. 20, is input to an AD (analogue-/digital) converter and a peak-detector circuit, which is shown in FIG. 21. The circuit is designated the reference numeral 450 in its entity and comprises an input terminal, through which the above-described output signal present at the output terminal 403 or the output terminal 447 is received.

The input terminal 451 is connected to ground through a resistor 452, and the input terminal 451 is further connected to the non-inverting input of an operational amplifier 453, the output of which is connected to the inverting input of the operational amplifier 453 through a feedback resistor 454, whereas the inverting input of the operational amplifier 453 is grounded through a resistor 455. The amplifier stage implemented by the operational amplifier 453 constitutes a single-decade amplifier, and a plurality of single-decade amplifier stages may be provided constituting sections of a multiple decade AD converter and peak-detector circuit. The output of the operational amplifier 453 is connected to an input of a multisection or multibit AD converter through a resistor 456. Each stage or section of the AD converter and peak detector is housed within a dotted-line boundary block, one of which is shown in great details and designated the reference numeral 457, whereas three additional stages, designated the reference numerals 458–460, are shown schematically.

The input signal supplied to the AD converter and peak-detector blocks 457–460 is presented to the non-inverting inputs of four comparators 461–464, which comparators 461–464 at their inverting inputs receive respective reference voltages generated from a positive supplier voltage by means of a resistance divider network comprising five resistors 465–469. The outputs of the comparators 461–464 are connected through pull-up resistors 470–473, respectively, to the above-mentioned, positive supply rail and further connected to respective Set inputs of a four-stage Set-Reset flip-flop 474, the Reset inputs of which are connected in parallel with reset terminals of corresponding Set-Reset flip-flops of the blocks 458–460 to a reset terminal 475.

The outputs of the individual stages of the Set-Reset flip-flop 474 are connected through resistors 476–479 to a inverting input of a summing-operational amplifier 481, the output of which is connected to the inverting input of the operational amplifier 481 through a feedback resistor 482. An additional inverting stage is provided comprising an operational amplifier 483, a feedback resistor 484 and an input resistor 485. The outputs of the individual stages of the four-stage Set-Reset flip-flop 484 are also connected to a digital encoding network 486, from which digital representations of the analogue input signals are presented for further digital signal processing.

The output of the operational amplifier 483, which output is connected to an output terminal 480, alternatively presents a wave-form processed, analogue representation of the analogue signal input to the AD converter and peak-detector circuit 460 through the input terminal 451. The output terminal 480 is connected to the aforementioned screw-terminal board of the electronic apparatus housed within the housing 189, which output signal is readily compatible with the signal processing carried out by the PC 88.

Reference is further made to example 5, in which the components of the electronic circuit 460 shown in FIG. 21 are listed.

In FIG. 22, a print out or diagramme from a test routine performed by means of a measuring system according to the present invention and implemented as discussed above with reference to the above description of a test bench setup and the above-described, electronic circuit is shown, which print out or diagramme illustrates the accumulated figures of particles within specific particle-dimension ranges. Thus, the total population of particles which were analyzed is divided into particle-dimension or size ranges, within which the number of particles present in the specimen are counted.

EXAMPLE 1

The electronic circuit shown in FIG. 17 was implemented from the following components:

the oscillator circuit block 209 was constituted by a 4060 integrated circuit, the crystal 210 was constituted by an oscillator crystal of the type 3M579, the NAND gates 211–214 were constituted by a single integrated, electronic circuit of the type 4011, the resistors 225 and 226 were 21.5 k$\Omega$ resistors, the operational amplifiers 215 and 240 were constituted by a single dual-operational amplifier of the type OPA2107, the resistor 216 was a 9.90 k$\Omega$ resistor, the capacitor 217 was a 82 pF capacitor, the resistors 218 and 219 were 1M$\Omega$ and 2.15 k$\Omega$ resistors, respectively, the capacitors 220 and 221 were 22 pF and 100 pF capacitors, respectively, the NPN transistor 222 was a BC 109 transistor, the resistor 223 was a 1.47 k$\Omega$ resistor, the capacitors 227, 228, 229, 230 and 245 were 0.1 $\mu$F capacitors, the resistor 242 was a 2.15 k$\Omega$ resistor, the resistor 243 was a 1 kΩ resistor,
the capacitors 244 and 246 were 10 μF capacitors,
the resistor 241 was a 5.62 kΩ resistor,
the capacitor 239 was a 820 pF capacitor,
the transformer 238 was a 1:1 transformer,
the relay 234 was a relay of the type SD2-16,
the resistors 249a and 249b were 12.1 kΩ resistors,
the operational amplifier 250 and 251 were constituted by a single dual-operational amplifier of the type OPA2107,
the diodes 252 and 253 were of the type BAT480,
the resistors 254–258 were 5.62 kΩ resistors,
the capacitors 259 and 260 were 0.1 μF capacitors,
the operational amplifier 260 of each of the sections 203, 204 and 207 was constituted by an operational amplifier of an integrated dual-operational amplifier of the type OPA2107,
the resistor 261 was a 2.87 kΩ resistor,
the resistor 262 was a 2.15 kΩ resistor,
the resistor 263 was an 11.0 kΩ resistor,
the capacitor 264 was an 8.2 nF capacitor,
the capacitor 265 was a 6.8 nF capacitor,
the capacitors 263 and 267 were 0.1 μF capacitors,
the operational amplifiers 270 and 280 were constituted by a single dual-operational amplifier of the type
the capacitor 271 was a 4.7 μF capacitor,
the resistor 272 was a 1.47 kΩ resistor,
the resistor 273 was a 14.7 kΩ resistor,
the capacitor 274 was a 100 pF capacitor,
the capacitor 275 was short-circuited by a direct wire connection,
the capacitors 276 and 277 were 0.1 μF capacitors
the resistor 281 was also short-circuited by a direct wire connection,
the resistor 282 was a 31.6 kΩ resistor,
the resistor 284 was a 3.48 kΩ resistor,
the capacitor 283 was a 100 pF capacitor,
the operational amplifier 290 was an operational amplifier of the type TL072,
the capacitor 291 was a 1 μF capacitor
the resistor 292 was a 21.5 kΩ resistor,
the resistor 293 was a 215 kΩ resistor, and
the capacitor 294 was a 82 pF capacitor.

EXAMPLE 2

The electronic circuit 300 shown in FIG. 18 was implemented from the following components:
The operational amplifier 302 was constituted by an integrated operational amplifier of the type 1458,
the resistor 303 was a 3.83 kΩ resistor
the resistor 304 was a 4.22 kΩ resistor,
the capacitor 305 was a 4.7 nF capacitor,
the capacitor 306 was a 2.7 nF capacitor,
the comparators 307 and 308 were constituted by a single integrated comparator circuit of the type TCL3704,
the operational amplifiers 309 and 310 were implemented by 1458 integrated operational amplifiers,
the resistors 311 and 312 were 19.6 kΩ resistors,
the resistors 313 and 314 were 10 kΩ linear potentiometers,
the capacitors 315 and 316 were 10 μF capacitors,
the NAND gates 317–321 were implemented by 4011 integrated electronic circuits,
the NOR gate 322 was implemented by a 4001 integrated electronic circuit,
the LED 324 was a light-emitting diode,
the resistor 326 was a 560Ω resistor, the operational amplifier 325 was an operational amplifier of the type LM339,
the timer circuits 330–333 were constituted by integrated electronic circuits of the type 4538,
the comparator 334 was implemented by an integrated electronic circuit of the type TCL3704,
the resistors 335 and 336 were 5.11 kΩ resistors,
the capacitors 337 and 339 were 10 μF capacitors,
the zener diode 338 was a zener diode of the type BAT85,
the resistor 340 was a 3.3 kΩ resistor,
the resistor 341 was a
10 kΩ linear potentiometer,
the capacitor 342 was a 100 nF capacitor,
the resistor 343 was a 100 kΩ resistor,
the resistor 344 was a 1.8 kΩ resistor,
the capacitors 345 and 346 were 10 nF capacitors,
the resistor 347 was a 100 kΩ resistor,
the capacitor 348 was a 100 nF capacitor,
the NAND gates 349 and 360 were constituted by NAND gates of the type 4011.

EXAMPLE 3

The electronic circuit 360 shown in FIG. 19 was implemented from the following components:
The operational amplifiers 361 and 362 were constituted by a single dual-integrated operational amplifier of the type OPA2107,
the operational amplifiers 363 and 364 were constituted by a dual-integrated operational amplifier of the type HA5222,
the operational amplifier 365 was constituted by an integrated operational amplifier of the type AD845,
the capacitors 366a and 366b were constituted by 0.1 μF and 10 μF capacitors, respectively,
the inductors 367 and 368 were constituted by a common-mode noise-rejection coil,
the capacitors 369 and 370 were 10 nF capacitors,
the capacitors 372 and 373 were 0.1 μF capacitors
the resistor 374 was a 10 kΩ resistor,
the capacitors 375 and 376 were 0.1 μF and 10 μF capacitors, respectively,
the capacitor 377 was a 10 pF capacitor,
the resistor 378 was a 10 kΩ resistor,
the resistor 379 was a 1 kΩ resistor,
the resistor 380 was a 10 kΩ resistor,
the capacitor 381 was a 10 pF capacitor,
the capacitor 382 and 383 were 0.1 μF capacitors
the resistor 384 was a 1 kΩ resistor,
the resistor 385 was a 10 kΩ resistor,
the capacitor 386 was a 10 pF capacitor,
the capacitor 387 was 0.1 μF capacitor
the resistors 388 and 390 were 46.4 resistors
the resistor 389 was a 10 kΩ linear potentiometer,
the resistor 385 was a 10 kΩ resistor,
the resistor 396 was a 1 kΩ resistor,
the capacitor 397 was a 0.1 μF capacitor,
the capacitors 393 and 394 were 10 μF and 0.1 μF capacitors respectively,
the capacitors 391 and 392 were 10 μF and 0.1 μF capacitors respectively,
the resistor 398 was a 10 kΩ resistor,
the capacitor 399 was a 10 pF capacitor,
the resistor 400 was a 470Ω resistor.

EXAMPLE 4

The electronic circuit 420 shown in FIG. 20 was implemented from the following components:

The photo-multiplier tube 421 was constituted by a photo-multiplier tube of the type R928HA, YM7923, the resistors 422–431 were 330 kΩ resistors, the capacitors 432–434 were 22 nF capacitors the operational amplifier 435 was implemented by an integrated operational amplifier of the type OPA627, the resistor 436 was a 1 kΩ resistor, the resistor 437 was a 1MΩ resistor, the capacitor 438 was a 15 pF capacitor the resistor 439 was a 110 kΩ resistor, the resistor 440 was a 10 kΩ resistor, the capacitors 443 and 445 were 100 nF capacitors, and the capacitors 444 and 446 were 2.2 μF capacitors.

EXAMPLE 5

The electronic circuit 460 shown in FIG. 21 was implemented from the following components:

The operational amplifier 453 was constituted by an integrated operational amplifier of the type AD845, the resistor 452 was omitted, the resistor 454 was a 3.16 kΩ resistor, the resistor 465 was a 348Ω resistor, the resistors 456 and 465 were constituted by short-circuiting connections, the resistor 465 was a 1.00 kΩ resistor, the resistor 467 was a 909Ω resistor the resistor 468 was a 825Ω resistor, the resistor 469 was a 750Ω resistor the comparators 461–464 were constituted by integrated electronic comparator circuits of the type TCL3704, the resistors 470–473 were constituted by 33 kΩ resistors, the integrated eletronic circuit 474 was of the type 4044 the resistors 476–479 were 100 kΩ resistors, the operational amplifiers 481 and 483 were implemented by a single dual-integrated operational amplifier of the type NE5512, the resistor 482 was a 1.00 kΩ resistor connected in parallel with a 12.1 kΩ resistor, the resistor 485 was constituted by a 10.0 kΩ resistor and the resistor 484 was constituted by a 10.0 kΩ resistor.

In the foregoing an apparatus is described, which makes is possible in a new and unique way to analyze particles suspended in a liquid, which particles are of a kind or are prepared or proofed in such a manner that they, when exposed to radiation, emit radiation characteristic of the particles. In the preferred embodiments, the apparatus is particularly suited for analyzing small, biological cells, e.g. lymphocytes of a magnitude of the order of 8–15 μm, by means of fluorescence spectrometry. The commercially available, prior art apparatuses having a corresponding field of application are far more complicated. Since the apparatus according to the invention is based upon completely novel principles and techniques, the invention comprises numerous subinventions, which in combination provide the best possible results. However, a number of these subinventions may also be considered independent inventions, which may be utilized in connection with other apparatuses or within other fields of the technique. Thus the above-described consecutive arrangement of two planar electrodes at the surface of a flow passage may be utilized as a general principle for counting and determining the size of particles suspended in a liquid. This type of analysis does not presuppose that the flow passage has been provided in an opening cuvette including two parts or body members.

Furthermore, the above-described agitating wire may be used independently in any narrow feeding passage for particles suspended in a liquid, by which application it is desired to avoid the particles from adhering to the surface of the feeding passage or to avoid agglomeration of the particles.

Moreover, the utilization, as a reflecting mirror area, of the second electrode arranged consecutively at the surface of a flow passage may be utilized generally in connection with a flash lamp as described above. A principle, by which a flash lamp is actuated on the basis of a measurement of conductivity, has been described by Kachel et al in The Journal of Histochemistry and Cytochemistry, vol. 27, no. 1, p. 335–341, 1979, but this principle relates to an essentially different field of application, viz. for a flow microscope, in which relevant particles are illuminated and visually registered, or as an image storage system, in which cells are photographed for the purpose of subsequent, morphologically image analyzing. Also focusing of the particles is used by forcing the particles through an aperture, whereas the laminar flow of an elongated flow passage is utilized according to the present invention.

Furthermore, it should be noted that the above-described hose pump according to the invention may also be used in other fields of application, in which a more accurate liquid dosage is intended than previously possible by means of the prior art.

Furthermore, it should be noted that the above-described piston pump according to the invention may also be used in other fields of application, in which a more accurate liquid dosage is intended than previously possible by means of the prior art.

Although, the present invention has been described with reference to the drawings illustrating advantageous and preferred embodiments of the invention and subinventions thereof, the above-given description is by no way to be construed limiting the protective scope of the present invention and subinventions thereof. Thus, numerous modifications and alternatives are readily perceivable to persons having ordinary skill in the art and are consequently to be considered part of the present invention and subinventions thereof.

I claim:

1. An apparatus for analyzing particles suspended in a fluid medium, said particles being capable of emitting radiation characteristic of said particles when exposed to radiation, and comprising:

a cuvette, in which an elongated flow area having the shape of a passage is provided for guiding said fluid medium in a first direction through said elongated flow area of said cuvette, means for feeding said fluid medium to said elongated flow area, means for discharging said fluid medium from said elongated flow area, means for exposing said fluid medium to said radiation in a second direction defining an angle relative to said first direction, means for picking up at least part of said radiation characteristic of said particles and emitted by said particles when exposed to radiation, said cuvette comprising a first body member having a planar facial surface and a second body member having a planar facial surface, said first and second body members being movable
relative to one another between a first position, in
which said planar facial surfaces are positioned
closely adjoining one another, and a second position, in which said planar facial surfaces are positioned spaced apart, at least said facial surface of said first body member
being provided with an elongated groove defining
together with said adjoining facial surface of said
second body member said elongated flow area
having the shape of said passage when said body
members are in said first position, said means for feeding said fluid medium to said elongated flow area comprising an inlet provided in one
of said body members and extending from the exterior relative to said cuvette to an inlet aperture of
said elongated flow area, said means for discharging said fluid medium comprising an outlet provided in one of said body members and extending from an outlet aperture of said
elongated flow area to the exterior relative to said
cuvette, and at least one of said body members being transparent
to said radiation to which said fluid medium is
exposed and to said radiation emitted by said particles.

2. A method of analyzing particles suspended in a fluid medium by means of an apparatus according to claim 1, comprising the following steps:

feeding said fluid medium in which said particles are
suspended into said elongated flow area through
said means for feeding said fluid medium to said
elongated flow area, guiding said fluid medium in said first direction
through said elongated flow area of said cuvette, exposing said fluid medium in which said particles are
suspended to said radiation in a second direction
defining an angle relative to said first direction, picking up at least part of said radiation characteristic
of said particles and emitted by said particles when
exposed to radiation by means of said means for
picking up at least part of said radiation characteristic of said particles and emitted by said particles
when exposed to radiation, discharging said fluid from said elongated flow area
by means of said means for discharging said fluid
medium from said elongated flow area, and in case a blocking of said elongated flow area or of
said means for feeding said fluid medium to said
elongated flow area occurs, moving said first and
second body members to said second position so as
to expel said fluid medium from said elongated
flow area and further from said means for feeding
said fluid medium to said elongated flow area, and
thus eliminate said blocking.

3. An apparatus for analyzing particles suspended in a fluid medium, said particles being capable of emitting radiation characteristic of said particles when exposed to radiation, and comprising:

a cuvette, in which an elongated flow area is provided for guiding said fluid medium in a first direction through said elongated flow area of said cuvette, said elongated flow area constituting a capillary passage;

means for feeding said fluid medium to said elongated flow area;

means for discharging said fluid medium from said
elongated flow area;

means for exposing said fluid medium to said radiation in a second direction defining an angle relative
to said first direction;

means for picking up at least part of said radiation
characteristic of said particles and emitted by said
particles when exposed to radiation;

said cuvette comprising a first body member having a
planar facial surface and a second body member
having a planar facial surface;

said first and second body members being movable
relative t one another between a first position, in
which said planar facial surfaces are positioned
closely adjoining one another, and a second position, in which said planar facial surfaces are positioned spaced apart;

at least said facial surface of said first body member
being provided with an elongated grove defining
together with said adjoining facial surface of said
second body member said elongated flow area
having the shape of said passage when said body
members are in said first position;

said means for feeding said fluid medium to said elongated flow area comprising an inlet provided in one
of said body members and extending from the exterior relative to said cuvette to an inlet aperture of
said elongated flow area;

said means for discharging said fluid medium comprising an outlet provided in one of said body members and extending from an outlet aperture of said
elongated flow area to the exterior relative to said
cuvette; and at least one of said body members being transparent
to said radiation to which said fluid medium is
exposed and to said radiation emitted by said particles.

4. An apparatus according to claim 3, said capillary passage having the shape of a geometrical section of a rectilinear cylinder having a circular cross section of a radius of curvature of approximately 50 $\mu$m.

5. An apparatus for analyzing particles suspended in a fluid medium, said particles being capable of emitting radiation characteristic of said particles when exposed to radiation, and comprising:

a cuvette, in which an elongated flow area having the
shape of a passage is provided for guiding said fluid
medium in a first direction through said elongated
flow area of said cuvette;

means for feeding said fluid medium to said elongated
flow area;

means for discharging said fluid medium from said
elongated flow area;

means for exposing said fluid medium to said radiation in a second direction defining an angle relative
to said first direction;

means for picking up at least part of said radiation
characteristic of said particles and emitted by said
particles when exposed to radiation;

said cuvette comprising a first body member having a
planar facial surface and a second body member
having a planar facial surface;

said first and second body members being movable
relative to one another between a first position, in
which said planar facial surfaces are positioned
closely adjoining one another, and a second position, in which said planar facial surfaces are positioned spaced apart;

at least said facial surface of said first body member
being provided with an elongated groove defining together with said adjoining facial surface of said second body member said elongated flow area having the shape of said passage when said body members are in said first position;

said means for feeding said fluid medium to said elongated flow area comprising an inlet provided in one of said body members and extending from the exterior relative to said cuvette to an inlet aperture of said elongated flow area;

said means for discharging said fluid medium comprising an outlet provided in one of said body members and extending from an outlet aperture of said elongated flow area to the exterior relative to said cuvette;

at least one of said body members being transparent to said radiation to which said fluid medium is exposed and to said radiation emitted by said particles; and at least two electrodes for generating an electrical field through which said fluid medium is passed when guided through said elongated flow area.

6. An apparatus according to claim 5, said elongated flow area constituting a capillary passage.

7. An apparatus for analyzing particles suspended in a fluid medium, said particles being capable of emitting radiation characteristic of said particles when exposed to radiation, and comprising:

a cuvette, in which an elongated flow area having the shape of a passage is provided for guiding said fluid medium in a first direction through said elongated flow area of said cuvette;

means for feeding said fluid medium to said elongated flow area;

means for discharging said fluid medium from said elongated flow area;

means for exposing said fluid medium to said radiation in a second direction defining an angle relative to said first direction;

means for picking up at least part of said radiation characteristic of said particles and emitted by said particles when exposed to radiation;

said cuvette comprising a first body member having a planar facial surface and a second body member having a planar facial surface;

said first and second body members being movable relative to one another between a first position, in which said planar facial surfaces are positioned closely adjoining one another, and a second position, in which said planar facial surfaces are positioned spaced apart;

at least said facial surface of said first body member being provided with an elongated groove defining together with said adjoining facial surface of said second body member said elongated flow area having the shape of said passage when said body members are in said first position;

said means for feeding said fluid medium to said elongated flow area comprising an inlet provided in one of said body members and extending from the exterior relative to said cuvette to an inlet aperture of said elongated flow area;

said means for discharging said fluid medium comprising an outlet provided in one of said body members and extending from an outlet aperture of said elongated flow area to the exterior relative to said cuvette;

at least one of said body members being transparent to said radiation to which said fluid medium is exposed and to said radiation emitted by said particles;

at least two electrodes for generating an electrical field through which said fluid medium is passed when guided through said elongated flow area; and said electrodes being embedded within said first or second body member providing exposed electrode surfaces at said elongated flow area.

8. An apparatus according to claim 7, said elongated flow area constituting a capillary passage.

9. An apparatus according to claim 7, said electrodes being arranged in succession relative to said first direction for generating said electrical field having lines of flux extending at a part of said elongated flow area substantially homogeneously and substantially parallel with said first direction.

10. An apparatus according to claim 7, said electrodes being spaced apart at said elongated flow area defining a minimum spacing of approximately 0.08 mm.

11. An apparatus for analyzing particles suspended in a fluid medium, said particles being capable of emitting radiation characteristic of said particles when exposed to radiation, and comprising:

a cuvette, in which an elongated flow area having the shape of a passage is provided for guiding said fluid medium in a first direction through said elongated flow area of said cuvette;

means for feeding said fluid medium to said elongated flow area;

means for discharging said fluid medium from said elongated flow area;

means for exposing said fluid medium to said radiation in a second direction defining an angle relative to said first direction;

means for picking up at least part of said radiation characteristic of said particles and emitted by said particles when exposed to radiation;

said cuvette comprising a first body member having a planar facial surface and a second body member having a planar facial surface;

said first and second body members being movable relative to one another between a first position, in which said planar facial surfaces are positioned closely adjoining one another, and a second position, in which said planar facial surfaces are positioned spaced apart;

at least said facial surface of said first body member being provided with an elongated groove defining together with said adjoining facial surface of said second body member said elongated flow area having the shape of said passage when said body members are in said first position;

said means for feeding said fluid medium to said elongated flow area comprising an inlet provided in one of said body members and extending from the exterior relative to said cuvette to an inlet aperture of said elongated flow area;

said means for discharging said fluid medium comprising an outlet provided in one of said body members and extending from an outlet aperture of said elongated flow area to the exterior relative to said cuvette;

at least one of said body members being transparent to said radiation to which said fluid medium is exposed and to said radiation emitted by said particles; and said mean for exposing said fluid medium to said radiation being constituted by a light source.

12. An apparatus according to claim 11, said light source generating light which is focused at a specific area of said elongated flow area.

13. An apparatus according to claim 12, further comprising a focusing means constituted by an objective lens arranged in direct optical communication with said cuvette for focusing said light at said specific area.

14. An apparatus for analyzing particles suspended in a fluid medium, said particles being capable of emitting radiation characteristic of said particles when exposed to radiation, and comprising:
- a cuvette, in which an elongated flow area having the shape of a passage is provided for guiding said fluid medium in a first direction through said elongated flow area of said cuvette;
- means for feeding said fluid medium to said elongated flow area;
- means for discharging said fluid medium from said elongated flow area;
- means for exposing said fluid medium to said radiation in a second direction defining an angle relative to said first direction;
- means for picking up at least part of said radiation characteristic of said particles and emitted by said particles when exposed to radiation;
- said cuvette comprising a first body member having a planar facial surface and a second body member having a planar facial surface;
- said first and second body members being movable relative to one another between a first position, in which said planar facial surfaces are positioned closely adjoining one another, and a second position, in which said planar facial surfaces are positioned spaced apart;
- at least said facial surface of said first body member being provided with an elongated groove defining together with said adjoining facial surface of said second body member said elongated flow area having the shape of said passage when said body members are in said first position;
- said means for feeding said fluid medium to said elongated flow area comprising an inlet provided in one of said body members and extending from the exterior relative to said cuvette to an inlet aperture of said elongated flow area;
- said means for discharging said fluid medium comprising an outlet provided in one of said body members and extending from an outlet aperture of said elongated flow area to the exterior relative to said cuvette;
- at least one of said body members being transparent to said radiation to which said fluid medium is exposed and to said radiation emitted by said particles;
- at least two electrodes for generating an electrical field through which said fluid medium is passed when guided through said elongated flow area; and
- said means for exposing said fluid medium to said radiation being constituted by a light source.

15. An apparatus according to claim 14, said electrodes being embedded within said first or second body member providing exposed electrode surfaces at said elongated flow area.

16. An apparatus according to claim 15, said electrodes being arranged in succession relative to said first direction for generating said electrical field having lines of flux extending a part of said elongated flow area substantially homogeneously and substantially parallel with said first direction.

17. An apparatus according to claim 14, said electrodes being spaced apart at said elongated flow area defining a minimum spacing of approximately 0.08 mm.

18. An apparatus for analyzing particles suspended in a fluid medium, said particles being capable of emitting radiation characteristic of said particles when exposed to radiation, and comprising:
- a cuvette, in which an elongated flow area having the shape of a passage is provided for guiding said fluid medium in a first direction through said elongated flow area of said cuvette;
- means for feeding said fluid medium to said elongated flow area;
- means for discharging said fluid medium from said elongated flow area;
- means for exposing said fluid medium to said radiation in a second direction defining an angle relative to said first direction;
- means for picking up at least part of said radiation characteristic of said particles and emitted by said particles when exposed to radiation;
- said cuvette comprising a first body member having a planar facial surface and a second body member having a planar facial surface;
- said first and second body members being movable relative to one another between a first position, in which said planar facial surfaces are positioned closely adjoining one another, and a second position, in which said planar facial surfaces are positioned spaced apart;
- at least said facial surface of said first body member being provided with an elongated groove defining together with said adjoining facial surface of said second body member said elongated flow area having the shape of said passage when said body members are in said first position;
- said means for feeding said fluid medium to said elongated flow area comprising an inlet provided in one of said body members and extending from the exterior relative to said cuvette to an inlet aperture of said elongated flow area;
- said means for discharging said fluid medium comprising an outlet provided in one of said body members and extending from an outlet aperture of said elongated flow area to the exterior relative to said cuvette;
- at least one of said body members being transparent to said radiation to which said fluid medium is exposed and to said radiation emitted by said particles;
- at least two electrodes for generating an electrical field through which said fluid medium is passed when guided through said elongated flow area;
- said means for exposing said fluid medium to said radiation being constituted by a light source, said light source generating light which is focused at a specific area of said elongated flow area;
- said electrodes and said specific area being arranged in succession relative to said first direction; and
- said electrodes being arranged upstream relative to said specific area.

19. An apparatus according to claim 18, further comprising a light reflecting means for reflecting said radiation emitted by said particles, when exposed to said light from said light source, to said means for picking up said radiation.

20. An apparatus for analyzing particles suspended in a fluid medium, said particles being capable of emitting radiation characteristic of said particles when exposed to radiation, and comprising:

a cuvette, in which an elongated flow area having the shape of a passage is provided for guiding said fluid medium in a first direction through said elongated flow area of said cuvette;

means for feeding said fluid medium to said elongated flow area;

means for discharging said fluid medium from said elongated flow area;

means for exposing said fluid medium to said radiation in a second direction defining an angle relative to said first direction;

means for picking up at least part of said radiation characteristic of said particles and emitted by said particles when exposed to radiation;

said cuvette comprising a first body member having a planar facial surface and a second body member having a planar facial surface;

said first and second body members being movable relative to one another between a first position, in which said planar facial surfaces are positioned closely adjoining one another, and a second position, in which said planar facial surfaces are positioned spaced apart;

at least said facial surface of said first body member being provided with an elongated groove defining together with said adjoining facial surface of said second body member said elongated flow area having the shape of said passage when said body members are in said first position; p1 said means for feeding said fluid medium to said elongated flow area comprising an inlet provided in one of said body members and extending from the exterior relative to said cuvette to an inlet aperture of said elongated flow area;

said means for discharging said fluid medium comprising an outlet provided in one of said body members and extending from an outlet aperture of said elongated flow area to the exterior relative to said cuvette;

at least one of said body members being transparent to said radiation to which said fluid medium is exposed and to said radiation emitted by said particles;

at least two electrodes for generating an electrical field through which said fluid medium is passed when guided through said elongated flow area;

said means for exposing said fluid medium to said radiation being constituted by a light source, said light source generating light which is focused at a specific area of said elongated flow area, said electrodes and said specific area being arranged in succession relative to said first direction;

said electrodes being arranged upstream relative to said specific area;

said light source being constituted by a flash; and a control means connected to said electrodes and to said flash for controlling the operation thereof in response to the detection of the particle passing through said electrical field so as to expose said particle to said light from said flash.

21. An apparatus according to claim 20, further comprising a light reflecting means for reflecting said radiation emitted by said particles, when exposed to said light from said light source, to said means for picking up said radiation.

22. An apparatus for analyzing particles suspended in a fluid medium, said particles being capable of emitting radiation characteristic of said particles when exposed to radiation, and comprising:

a cuvette, in which an elongated flow area having the shape of a passage is provided for guiding said fluid medium in a first direction through said elongated flow area of said cuvette;

means for feeding said fluid medium to said elongated flow area;

means for discharging said fluid medium from said elongated flow area;

means for exposing said fluid medium to said radiation in a second direction defining an angle relative to said first direction;

means for picking up at least part of said radiation characteristic of said particles and emitted by said particles when exposed to radiation;

said cuvette comprising a first body member having a planar facial surface and a second body member having a planar facial surface;

said first and second body members being movable relative to one another between a first position, in which said planar facial surfaces are positioned closely adjoining one another, and a second position, in which said planar facial surfaces are positioned spaced apart;

at least said facial surface of said first body member being provided with an elongated groove defining together with said adjoining facial surface of said second body member said elongated flow area having the shape of said passage when said body members are in said first position;

said means for feeding said fluid medium to said elongated flow area comprising an inlet provided in one of said body members and extending from the exterior relative to said cuvette to an inlet aperture of said elongated flow area;

said means for discharging said fluid medium comprising an outlet provided in one of said body members and extending from an outlet aperture of said elongated flow area to the exterior relative to said cuvette;

at least one of said body members being transparent to said radiation to which said fluid medium is exposed and to said radiation emitted by said particles;

at least two electrodes for generating an electrical field through which said fluid medium is passed when guided through said elongated flow area;

said electrodes being embedded within said first or second body member providing exposed electrode surfaces at said elongated flow area;

said electrodes and a specific area of said elongated flow area being arranged in succession relative to said first direction;

said electrodes being arranged upstreams relative to said specific area;

means for exposing said fluid medium to said radiation constituted by a light source being further constituted by a flash; and a control means connected to said electrodes and to said flash for controlling the operation thereof in response to the detection of the particle passing through said electrical field so as to expose said particle to said light from said flash.

23. An apparatus according to claim 22, said light reflecting means being constituted by one of said exposed electrode surfaces.

24. An apparatus according to claim 23, said exposed electrode surface constituting said light reflecting means being arranged at said elongated groove.

25. An apparatus for analyzing particles suspended in a fluid medium, said particles being capable of emitting radiation characteristic of said particles when exposed to radiation, and comprising:
   a cuvette, in which an elongated flow area having the shape of a passage is provided for guiding said fluid medium in a first direction through said elongated flow area of said cuvette;
   means for feeding said fluid medium to said elongated flow area;
   means for discharging said fluid medium from said elongated flow area;
   means for exposing said fluid medium to said radiation in a second direction defining an angle relative to said first direction;
   means for picking up at least part of said radiation characteristic of said particles and emitted by said particles when exposed to radiation;
   said cuvette comprising a first body member having a planar facial surface and a second body member having a planar facial surface;
   said first and second body members being movable relative to one another between a first position, in which said planar facial surfaces are positioned closely adjoining one another, and a second position, in which said planar facial surfaces are positioned spaced apart;
   at least said facial surface of said first body member being provided with an elongated groove defining together with said adjoining facial surface of said second body member said elongated flow area having the shape of said passage when said body members are in said first position;
   said means for feeding said fluid medium to said elongated flow area comprising an inlet provided in one of said body members and extending from the exterior relative to said cuvette to an inlet aperture of said elongated flow area;
   said means for discharging said fluid medium comprising an outlet provided in one of said body members and extending from an outlet aperture of said elongated flow area to the exterior relative to said cuvette;
   at least one of said body members being transparent to said radiation to which said fluid medium is exposed and to said radiation emitted by said particles;
   an agitating means constituted by a wire and a wire rotating means, said wire being arranged extending through said means for feeding said fluid medium to said elongated flow area and at least partially into said elongated flow area, said wire being rotated relative to its rotational axis by means of said wire rotating means so as, to any substantial extent, to eliminate the risk of blocking said feeding means and said elongated flow area.

26. An apparatus according to claim 25, said wire having a circular cross section or alternatively a non-circular cross section, such as a polygonal cross section.

27. An apparatus according to claim 26, said wire being of a material which is compatible with said fluid medium and which does not swell to any substantial extent in water, such as nylon, polypropylene, polycarbonate, or Teflon TM.

28. An apparatus for analyzing particles suspended in a fluid medium, said particles being capable of emitting radiation characteristic of said particles when exposed to radiation, and comprising:
   a cuvette, in which an elongated flow area having the shape of a passage is provided for guiding said fluid medium in a first direction through said elongated flow area of said cuvette;
   means for feeding said fluid medium to said elongated flow area;
   means for discharging said fluid medium from said elongated flow area;
   means for exposing said fluid medium to said radiation in a second direction defining an angle relative to said first direction;
   means for picking up at least part of said radiation characteristic of said particles and emitted by said particles when exposed to radiation;
   said cuvette comprising a first body member having a planar facial surface and a second body member having a planar facial surface;
   said first and second body members being movable relative to one another between a first position, in which said planar facial surfaces are positioned closely adjoining one another, and a second position, in which said planar facial surfaces are positioned spaced apart;
   at least said facial surface of said first body member being provided with an elongated groove defining together with said adjoining facial surface of said second body member said elongated flow area having the shape of said passage when said body members are in said first position;
   said means for feeding said fluid medium to said elongated flow area comprising an inlet provided in one of said body members and extending from the exterior relative to said cuvette to an inlet aperture of said elongated flow area;
   said means for discharging said fluid medium comprising an outlet provided in one of said body members and extending from an outlet aperture of said elongated flow area to the exterior relative to said cuvette;
   at least one of said body members being transparent to said radiation to which said fluid medium is exposed and to said radiation emitted by said particles; and
   a means for feeding a diluent to said elongated flow area.

29. An apparatus according to claim 28, further comprising means for controlling the supply of said diluent to said elongated flow area.

30. An apparatus for analyzing particles suspended in a fluid medium, said particles being capable of emitting radiation characteristic of said particles when exposed to radiation, and comprising:
   a cuvette, in which an elongated flow area having the shape of a passage is provided for guiding said fluid medium in a first direction through said elongated flow area of said cuvette;
   means for feeding said fluid medium to said elongated flow area;
   means for discharging said fluid medium from said elongated flow area;

means for exposing said fluid medium to said radiation in a second direction defining an angle relative to said first direction;

means for picking up at least part of said radiation characteristic of said particles and emitted by said particles when exposed to radiation;

said cuvette comprising a first body member having a planar facial surface and a second body member having a planar facial surface;

said first and second body members being movable relative to one another between a first position, in which said planar facial surfaces are positioned closely adjoining one another, and a second position, in which said planar facial surfaces are positioned spaced apart;

at least said facial surface of said first body member being provided with an elongated groove defining together with said adjoining facial surface of said second body member said elongated flow area having the shape of said passage when said body members are in said first position;

said means for feeding said fluid medium to said elongated flow area comprising an inlet provided in one of said body members and extending from the exterior relative to said cuvette to an inlet aperture of said elongated flow area;

said means for discharging said fluid medium comprising an outlet provided in one of said body members and extending from an outlet aperture of said elongated flow area to the exterior relative to said cuvette;

at least one of said body members being transparent to said radiation to which said fluid medium is exposed and to said radiation emitted by said particles;

at least two electrodes for generating an electrical field through which said fluid medium is passed when guided through said elongated flow area;

said means for exposing said fluid medium to said radiation being constituted by a light source, said light source generating light which is focused at a specific area of said elongated flow area;

said electrodes and said specific area being arranged in succession relative to said first direction;

said light source being constituted by a flash;

a control means connected to said electrodes and to said flash and controlling the operation thereof in response to the detection of the particle passing through said electrical field so as to expose said particles to said light from said flash;

a means for feeding a diluent to said elongated flow area;

means for controlling the supply of said diluent to said elongated flow area and;

said means for controlling the supply of diluent to said elongated flow area being connected to and being controlled by said control means.

31. An apparatus according to claim 30, said means for feeding said diluent to said elongated flow area being arranged upstream relative to said electrodes, and said control means controlling said means for controlling the supply of said diluent to said elongated flow area so as to provide a predetermined particle-flow rate through said elongated flow area.

32. An apparatus according to claim 30, said means for feeding said diluent to said elongated flow area being arranged upstream relative to said electrodes, and said control means controlling said means for controlling the supply of said diluent to said elongated flow area so as to present said particles to said exposure means individually and at a rate lower than a predetermined maximum rate, such as a rate of 100 particles per second.

33. An apparatus for analyzing particles suspended in a fluid medium, said particles being capable of emitting radiation characteristic of said particles when exposed to radiation, and comprising:

a cuvette, in which an elongated flow area having the shape of a passage is provided for guiding said fluid medium in a first direction through said elongated flow area of said cuvette;

means for feeding said fluid medium to said elongated flow area;

means for discharging said fluid medium from said elongated flow area;

means for exposing said fluid medium to said radiation in a second direction defining an angle relative to said first direction;

means for picking up at least part of said radiation characteristic of said particles and emitted by said particles when exposed to radiation;

said cuvette comprising a first body member having a planar facial surface and a second body member having a planar facial surface;

said first and second body members being movable relative to one another between a first position, in which said planar facial surfaces are positioned closely adjoining one another, and a second position in which said planar facial surfaces are positioned spaced apart;

at least said facial surface of said first body member being provided with an elongated groove defining together with said adjoining facial surface of said second body member said elongated flow area having the shape of said passage when said body members are in said first position;

said means for feeding said fluid medium to said elongated flow area comprising an inlet provided in one of said body members and extending from the exterior relative to said cuvette to an inlet aperture of said elongated flow area;

said means for discharging said fluid medium comprising an outlet provided in one of said body members and extending from an outlet aperture of said elongated flow area to the exterior relative to said cuvette;

at least one of said body members being transparent to said radiation to which said fluid medium is exposed and to said radiation emitted by said particles; and a flow control means for controlling the flow of said fluid medium through said elongated flow area.

34. An apparatus according to claim 33, said flow control means being constituted by a pump connected to said means for discharging said fluid medium from said elongated flow area and generating a substantially constant flow rate of said fluid medium through said elongated flow area.

35. An apparatus for analyzing particles suspended in a fluid medium, said particles being capable of emitting radiation characteristic of said particles when exposed to radiation, and comprising:

a cuvette, in which an elongated flow area having the shape of a passage is provided for guiding said fluid medium in a first direction through said elongated flow area of said cuvette;

means for feeding said fluid medium to said elongated flow area;

means for discharging said fluid medium from said elongated flow area;

means for exposing said fluid medium to said radiation in a second direction defining an angle relative to said first direction;

means for picking up at least part of said radiation characteristic of said particles and emitted by said particles when exposed to radiation;

said cuvette comprising a first body member having a planar facial surface and a second body member having a planar facial surface;

said first and second body members being movable relative to one another between a first position, in which said planar facial surfaces are positioned closely adjoining one another, and a second position, in which said planar facial surfaces are positioned spaced apart;

at least said facial surface of said first body member being provided with an elongated groove defining together with said adjoining facial surface of said second body member said elongated flow area having the shape of said passage when said body members are in said first position;

said means for feeding said fluid medium to said elongated flow area comprising an inlet provided in one of said body members and extending from the exterior relative to said cuvette to an inlet aperture of said elongated flow area;

said means for discharging said fluid medium comprising an outlet provided in one of said body members and extending from an outlet aperture of said elongated flow area to the exterior relative to said cuvette;

at least one of said body members being transparent to said radiation to which said fluid medium is exposed and to said radiation emitted by said particles; and a spring-loading means actuating at least one of said body members by a spring force perpendicular to said facial surfaces of said body members.

36. An apparatus according to claim 35, said first and second body members being movable relative to one another by parallel displacing at least one of said two body members in a direction perpendicular to said planar facial surfaces of said body members.

37. An apparatus according to claim 35, further comprising a stop means receiving said spring-loaded body member when said body members are moved to said second position so as to maintain said spring-loaded body member in a well-defined position.

38. An apparatus for analyzing particles suspended in a fluid medium, said particles being capable of emitting radiation characteristic of said particles when exposed to radiation, and comprising:

a cuvette, in which an elongated flow area having the shape of a passage is provided for guiding said fluid medium in a first direction through said elongated flow area of said cuvette;

means for feeding said fluid medium to said elongated flow area;

means for discharging said fluid medium from said elongated flow area;

means for exposing said fluid medium to said radiation in a second direction defining an angle relative to said first direction;

means for picking up at least part of said radiation characteristic of said particles and emitted by said particles when exposed to radiation;

said cuvette comprising a first body member having a planar facial surface and a second body member having a planar facial surface;

said first and second body members being movable relative to one another between a first position, in which said planar facial surfaces are positioned closely adjoining one another, and a second position, in which said planar facial surfaces are positioned spaced apart;

at least said facial surface of said first body member being provided with an elongated groove defining together with said adjoining facial surface of said second body member said elongated flow area having the shape of said passage when said body members are in said first position;

said means for feeding said fluid medium to said elongated flow area comprising an inlet provided in one of said body members and extending from the exterior relative to said cuvette to an inlet aperture of said elongated flow area;

said means for discharging said fluid medium comprising an outlet provided in one of said body members and extending from an outlet aperture of said elongated flow area to the exterior relative to said cuvette;

at least one of said body members being transparent to said radiation to which said fluid medium is exposed and to said radiation emitted by said particles; and a means for conducting a rinsing liquid to said planar facial surfaces of said body members when said body members are in said second position.

39. An apparatus according to claim 39, further comprising a rotatable rinsing brush, which is movable relative to said body members across said planar facial surfaces thereof when said body members are in said second position so as to mechanically clean said planar facial surfaces.

40. An apparatus for analyzing particles suspended in a fluid medium, said particles being capable of emitting radiation characteristic of said particles when exposed to radiation, and comprising:

a cuvette, in which an elongated flow area having the shape of a passage is provided for guiding said fluid medium in a first direction through said elongated flow area of said cuvette;

means for feeding said fluid medium to said elongated flow area;

means for discharging said fluid medium from said elongated flow area;

means for discharging said fluid medium from said elongated flow area;

means for exposing said fluid medium to said radiation in a second direction defining an angle relative to said first direction;

means for picking up at least part of said radiation characteristic of said particles and emitted by said particles when exposed to radiation;

said cuvette comprising a first body member having a planar facial surface and a second body member having a planar facial surface;

said first and second body members being movable relative to one another between a first position, in which said planar facial surfaces are positioned closely adjoining one another, and a second position, in which said planar facial surfaces are positioned spaced apart;

at least said facial surface of said first body member being provided with an elongated groove defining together with said adjoining facial surface of said second body member said elongated flow area having the shape of said passage when said body members are in said first position;

said means for feeding said fluid medium to said elongated flow area comprising an inlet provided in one of said body members and extending from the exterior relative to said cuvette to an inlet aperture of said elongated flow area;

said means for discharging said fluid medium comprising an outlet provided in one of said body members and extending from an outlet aperture of said elongated flow area to the exterior relative to said cuvette;

at least one of said body members being transparent to said radiation to which said fluid medium is exposed and to said radiation emitted by said particles; and said apparatus being adapted to carry out a flow-cytometrical analysis of fluorescent particles, in particular the size of the particles is within the range of approximately 8–15 $\mu$m.

* * * * *